United States Patent
Bell et al.

(10) Patent No.: US 6,579,886 B2
(45) Date of Patent: Jun. 17, 2003

(54) SELECTIVE IGLUR5 RECEPTOR ANTAGONISTS

(75) Inventors: Michael Gregory Bell, Indianapolis, IN (US); Michael Edward Le Tourneau, Indianapolis, IN (US); Michael John Martinelli, Indianapolis, IN (US); Mark Alan Winter, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/148,712

(22) PCT Filed: Dec. 12, 2000

(86) PCT No.: PCT/US00/32450

§ 371 (c)(1),
(2), (4) Date: Sep. 3, 2002

(87) PCT Pub. No.: WO01/46173

PCT Pub. Date: Jun. 28, 2001

(65) Prior Publication Data

US 2003/0055081 A1 Mar. 20, 2003

Related U.S. Application Data

(60) Provisional application No. 60/171,436, filed on Dec. 22, 1999.

(51) Int. Cl.$^7$ .................. C07D 217/06; A61K 31/47
(52) U.S. Cl. .................. 514/307; 514/231.5; 544/128; 546/146
(58) Field of Search .................. 544/128; 546/146; 514/231.5, 307

(56) References Cited

U.S. PATENT DOCUMENTS

| | | | | |
|---|---|---|---|---|
| 5,356,902 A | 10/1994 | Ornstein | ............... | 514/307 |
| 5,446,051 A | 8/1995 | Ornstein | ............... | 514/307 |
| 5,670,516 A | 9/1997 | Arnold et al. | ............... | 514/307 |
| 5,675,008 A | 10/1997 | Bertsch et al. | ............... | 546/147 |
| 5,767,117 A | 6/1998 | Moskowitz | ............... | 514/219 |

FOREIGN PATENT DOCUMENTS

| | | |
|---|---|---|
| WO | WO 98/45270 | 10/1998 |
| WO | WO 01/01972 | 1/2001 |
| WO | WO 01/02367 | 1/2001 |

OTHER PUBLICATIONS

Paul L. Ornstein, et al., Structure–Activity Studies of 6–Substituted Decahydroisoquinoline–3–carboxylic Acid AMPA Receptor Antagonists. 2. Effects of Distal Acid Bioisosteric Substitution, Absolute Stereochemical Preferences, and in Vivo Activity, J. Med. Chem., vol. 39, No. 11, pp. 2232–2244 (1996).

Proctoer, et al., "Possible role of GluR5 glutamate receptors in spinal nociceptive processing in the anaesthetized rat," Journal of Physiology, XX, XX, vol. 504P, pp. 101P–102P; XP002108296; (1997).

Nikam, et al., "The search of AMPA/Gly (N) receptor antagonists," Drugs Future, vol. 24, No. 10, pp. 1107–1124; XP000997758; (1999).

O'Neill, et al., "Decahydroisoquinolines: novel competitive AMPA/kainite antagonists with neuroprotective effects in global cerebral ischaemia," Nueropharmacology, Oct.–Nov., 1998, 37 (10–11); pp. 1211–1222; XP000997636Nikam, et al., "The search for AMPA/Gly (N) receptor antagonists," Drugs Future, vol. 24, No. 10, pp. 1107–1124; XP000997758; (1999).

Procter, et al., "Actions of kainite and AMPA selective glutamate receptor ligands on noniceptive processing in the spinal cord," Neuropharmacoly, Oct.–Nov., 1998, 37 (10–11); pp. 1287–1297; XP000997628; (1998).

Bleakman, "Kainate receptor pharmacology and physiology," Cellular and Molecular Life Sciences, 56/7–8 (558–566); XP000990931.

Simmons, et al., "Kainate GluR5 receptor subtype mediates the nociceptive response to formalin in the rat," Neuropharmacology, 37(1), pp. 25–36; XP000997629 (1998).

Database Medline "Online", US National Library of Medicine (NLM), Bethesda, MD, US; Mitsikostas D.D., et al, "Non–NMDA glutamate receptors modulate capsaicin induced c–fos expression within trigeminal nucleus caudalis," retrieved from Dialog, Database accession No. 10003939; XP002165715 abstract & British Journal of Pharmacology, Jun., 1999, 127 (3) pp. 623–630.

*Primary Examiner*—Zinna Northington Davis
(74) *Attorney, Agent, or Firm*—Alexander Wilson; Nelsen L. Lentz

(57) ABSTRACT

The present invention provides compounds of formula (I): wherein W represents hydrogen, $C_1$–$C_4$ alkyl, —$CH_2CO_2H$, or $CO_2H$; and X represents hydrogen, $C_1$–$C_4$ alkyl, —$CH_2CO_2H$, or $CO_2H$; with the proviso that at least one of W or X must be other than hydrogen; or a prodrug or a pharmaceutically acceptable salt thereof; which are useful for treating migraine.

21 Claims, No Drawings

SELECTIVE IGLUR5 RECEPTOR ANTAGONISTS

This is a provisional application No. 60/171,436, filed on Dec. 22, 1999.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathways in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). Molecular biological studies have established that AMPA receptors are composed of subunits ($GluR_1$-$GluR_4$), which can assemble to form functional ion channels. Five kainate receptors have been identified which are classified as either High Affinity (KA1 and KA2) or Low Affinity ($GluR_5$, $GluR_6$, and $GluR_7$). Bleakman et al., *Molecular Pharmacology*, 49, No.4, 581,(1996).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacol. Sci.*, 14, 13 (1993). Both types of receptors appear not only to mediate normal synaptic transmission along excitatory pathways, but also to participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of neurological disorders and conditions. The medical consequences of such neuronal degeneration makes the abatement of these degenerative neurological processes an important therapeutic goal.

Excitatory amino acid excitotoxicity has been implicated in the pathophysiology of numerous neurological disorders. For example, excitotoxicity has been linked with the etiology of cerebral deficits subsequent to cardiac bypass surgery and grafting, stroke, cerebral ischemia, spinal cord lesions resulting from trauma or inflammation, perinatal hypoxia, cardiac arrest, and hypoglycemic neuronal damage. In addition, excitotoxicity has been implicated in chronic neurodegenerative conditions including Alzheimer's Disease, Huntington's Chorea, inherited ataxias, AIDS-induced dementia, amyotrophic lateral sclerosis, idiopathic and drug-induced Parkinson's Disease, as well as ocular damage and retinopathy. Other neurological disorders implicated with excitotoxicity and/or glutamate dysfunction include muscular spasticity, tremors, drug tolerance and withdrawal, brain edema, convulsive disorders including epilepsy, depression, anxiety and anxiety related disorders such as post-traumatic stress syndrome, tardive dyskinesia, and psychosis related to depression, schizophrenia, bipolar disorder, mania, and drug intoxication or addiction. In addition, it has also been reported that excitatory amino acid excitotoxicity participates in the etiology of acute and chronic pain states including severe pain, intractable pain, neuropathic pain, and post-traumatic pain.

The use of a neuroprotective agent, such as an excitatory amino acid receptor antagonist, is believed to be useful in treating or preventing these disorders and/or reducing the amount of neurological damage associated with these disorders. Excitatory amino acid receptor antagonists may also be useful as analgesic agents.

Early theories regarding the pathophysiology of migraine have been dominated since 1938 by the work of Graham and Wolff (*Arch. Neurol. Psychiatry*, 39, 737–63 (1938)). They proposed that the cause of migraine headache is vasodilatation of extracranial vessels. This view is supported by knowledge that ergot alkaloids and sumatriptan contract cephalic vascular smooth muscle and are effective in the treatment of migraine. Sumatriptan is a hydrophilic agonist at the serotonin 5-HT-1-like receptors and does not cross the blood-brain barrier (Humphrey, et al., *Ann. NY Acad. Sci.*, 600, 587–600 (1990)). Consequently, several series of compounds said to be useful for the treatment of migraine, have been developed to optimize the $5-HT_1$-like mediated vasoconstrictive activity of sumatriptan. However, sumatriptan's contraindications, including coronary vasospasm, hypertension, and angina are also products of its vasoconstrictive activity (Macintyre, P. D., et al., *British Journal of Clinical Pharmacology*, 34, 541–546 (1992); Chester, A. H., et al., *Cardiovascular Research*, 24, 932–937 (1990); Conner, H. E., et al., *European Journal of Pharmacology*, 161, 91–94 (1990)).

While the vascular mechanism for migraine has gained wide acceptance, there is not total agreement as to its validity. Moskowitz, for example, has shown the occurrence of migraine headaches, independent of changes in vessel diameter (*Cephalalgia*, 12, 5–7, (1992)). It is known that the trigeminal ganglion, and its associated nerve pathways, are associated with painful sensations from the face such as headache, in particular migraine. Moskowitz proposed that unknown triggers stimulate the trigeminal ganglia which innervate vasculature within cephalic tissue, giving rise to the release of vasoactive neuropeptides from axons innervating the vasculature. These neuropeptides initiate a series of events leading to neurogenic inflammation of the meninges, a consequence of which is pain. This neurogenic inflammation is blocked by sumatriptan at doses similar to those required to treat acute migraine in humans. However, such doses of sumatriptan, as stated, are associated with contraindications as a result of sumatriptan's attendant vasoconstrictive properties.(see supra.)

$5-HT_{1D}$ receptors have been implicated as mediating the blockade of neurogenic protein extravasation. (*Neurology*, 43(suppl. 3), S16–S20 (1993)). In addition, it has been reported that $\alpha_2$, $H_3$, m-opioid and somatostatin receptors may also be located on trigeminovascular fibers and may block neurogenic plasma extravasation (Matsubara et al., *Eur. J. Pharmacol.*, 224,145–150 (1992)). Weinshank et al. have reported that sumatriptan and several ergot alkaloids have a high affinity for the serotonin 5–$HT_{1F}$ receptor, suggesting a role for the 5–$HT_{1F}$ receptor in migraine (WO93/14201).

European Patent Application Publication No. 590789A1 and U.S. Pat. Nos. 5,446,051 and 5,670,516 disclose that certain decahydroisoquinoline derivative compounds are AMPA receptor antagonists and, as such, are useful in the treatment of many different conditions, including pain and migraine headache.

Recently, it has been reported that all five members of the kainate subtype, of ionotropic glutamate receptors, are expressed on rat trigeminal ganglion neurons. In particular, high levels of $GluR_5$ and KA2 have been observed. (Sahara et al., *The Journal of Neuroscience*, 17(17), 6611 (1997)). Simmons et al. reported that the kainate $GluR_5$ receptor subtype mediates the nociceptive response to formalin in a rat model of persistent pain.(*Neuropharmacology*, 37, 25 (1998). Further, WO98/45270 previously disclosed that antagonists selective for the $iGluR_5$ receptor are useful for the treatment of pain, including; severe, chronic, intractable, and neuropathic pain.

In accordance with the present invention, Applicants have discovered compounds that are antagonists of the $iGluR_5$ receptor subtype and which are surprisingly selective for the $iGluR_5$ receptor subtype. In addition, the compounds of the present invention are efficacious in an animal model of neurogenic inflammation and, thus, could be useful for the treatment of migraine. Such selective antagonists could address a long felt need for a safe and effective treatment for migraine, without attending side effects. The treatment of neurological disorders is hereby furthered. Furthermore, the diester prodrugs of the corresponding diacids have been found to possess substantially improved bioavailability as compared to the corresponding diacids.

The present invention provides compounds of formula I:

formula I

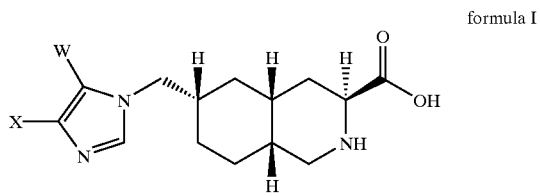

wherein

W represents hydrogen, $C_1$–$C_4$ alkyl, —$CH_2CO_2H$, or $CO_2H$; and

X represents hydrogen, $C_1$–$C_4$ alkyl, —$CH_2CO_2H$, or $CO_2H$;

with the proviso that at least one of W or X must be other than hydrogen;

or a prodrug or a pharmaceutically acceptable salt thereof.

The present invention further provides a method of treating migraine which comprises administering to a patient an effective amount of a compound of formula I or a pharmaceutically acceptable salt thereof.

In another embodiment, the present invention provides a method of treating or preventing a neurological disorder, or neurodegenerative condition, comprising administering to a patient in need thereof an effective amount of a compound of formula I or pharmaceutically acceptable salt thereof.

Examples of such neurological disorders, or neurodegenerative conditions, include: cerebral deficits subsequent to cardiac bypass surgery and grafting; stroke; cerebral ischemia; spinal cord lesions resulting from trauma or inflammation; perinatal hypoxia; cardiac arrest; hypoglycemic neuronal damage; Alzheimer's Disease; Huntington's Chorea; inherited ataxias; AIDS-induced dementia; amyotrophic lateral sclerosis; idiopathic and drug-induced Parkinson's Disease; ocular damage and retinopathy; muscular spasticity, tremors; drug tolerance and withdrawal; brain edema; convulsive disorders including epilepsy; depression; anxiety and anxiety related disorders such as post-traumatic stress syndrome; tardive dyskinesia; psychosis related to depression, schizophrenia, bipolar disorder, mania, and drug intoxication or addiction; and acute and chronic pain states including severe pain, intractable pain, neuropathic pain, and post-traumatic pain.

The invention further provides a process for preparing a compound of formula Id:

formula Id

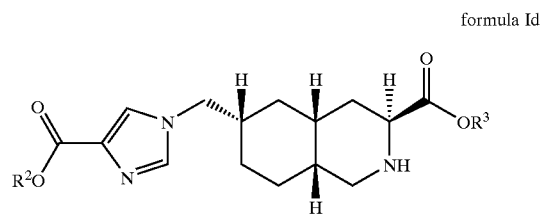

wherein $R^2$ and $R^3$ each independently represent $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, or $C_1$–$C_6$ alkyl-morpholine;

comprising combining a compound of structure (3a):

(3a)

wherein $R^2$ is defined as above, with a suitable base in a suitable solvent, followed by addition of a compound of structure (2):

(2)

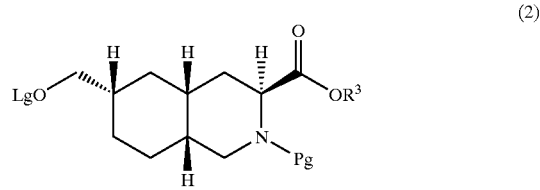

wherein $R^3$ is defined as above, Pg is a suitable nitrogen protecting group, and OLg is a suitable leaving group, followed by removal of the nitrogen protecting group.

The present invention further provides a compound of the formula:

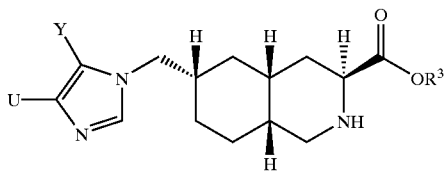

wherein

Y represents hydrogen, $C_1$–$C_4$ alkyl, —$CH_2CO_2R^1$, or $CO_2R^1$;

U represents hydrogen, $C_1$–$C_4$ alkyl, —$CH_2CO_2R^2$, or $CO_2R^2$; and $R^1$, $R^2$ and $R^3$ each independently represent hydrogen, $C_1$–$C_{20}$ alkyl, $C_2$–$C_6$ alkenyl, $C_1$–$C_6$ alkylaryl, $C_1$–$C_6$ alkyl($C_3$–$C_{10}$)cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, or $C_1$–$C_6$ alkyl-morpholine;

or a pharmaceutically acceptable salt thereof, with the proviso that at least one of Y or U is other than hydrogen or $C_1$–$C_4$ alkyl, and with the further proviso that at least one of $R^1$, $R^2$ or $R^3$ is other than hydrogen.

In addition, the invention provides pharmaceutical compositions of compounds of formula I, including the hydrates thereof, comprising, as an active ingredient, a compound of formula I in combination with a pharmaceutically acceptable carrier, diluent or excipient. This invention also encompasses novel intermediates, and processes for the synthesis of the compounds of formula I.

According to another aspect, the present invention provides the use of a compound of formula I, or a pharmaceutically acceptable salt thereof as defined hereinabove for the manufacture of a medicament for treating migraine.

According to yet another aspect, the present invention provides the use of a compound of formula I or a pharmaceutically acceptable salt thereof as defined hereinabove for treating migraine.

The present invention provides a method for the treatment of migraine which can be demonstrated by a particular mechanism of action, inhibition of neurogenic dural protein extravasation. By treating a migraineur with a compound of formula I which is a selective antagonist of the iGluR$_5$ receptor, the neurogenic extravasation which mediates migraine is inhibited without the attending side effects of agents designed to optimize the 5-HT$_1$-like mediated vasoconstrictive activity of sumatriptan.

As used herein, the term "prodrug" refers to a compound of the formula I which has been structurally modified such that in vivo the prodrug is converted into the parent compound of the formula I (for example, by hydrolytic, oxidative, reductive, or enzymatic cleavage). Such prodrugs may be, for example, metabolically labile ester or amide derivatives of the parent compound having a carboxylic acid group. It is to be understood that the present invention includes any such prodrugs, such as metabolically labile ester or amide derivatives of compounds of the formula I. Conventional procedures for the selection and preparation of suitable prodrugs are well known to one of ordinary skill in the art.

More specifically, examples of prodrugs of formula I which are understood to be included within the scope of the present invention are represented by formulas Ia, Ib and Ic below:

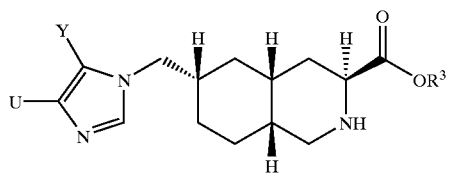

formula Ia

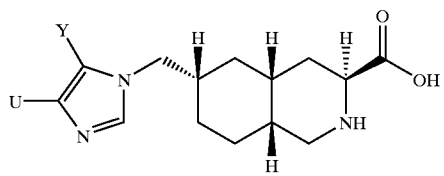

formula Ib

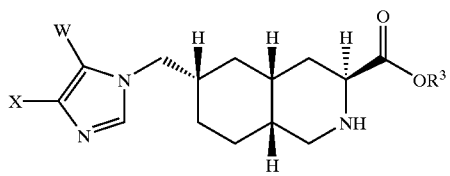

formula Ic wherein

W and X are as defined hereinabove;

Y represents hydrogen, $C_1$–$C_4$ alkyl, —$CH_2CO_2R^1$, or $CO_2R^1$;

U represents hydrogen, $C_1$–$C_4$ alkyl, —$CH_2CO_2R^2$, or $CO_2R^2$; and $R^1$, $R^2$ and $R^3$ each independently represent hydrogen, $C_1$–$C_{20}$ alkyl, $C_2$–$C_6$ alkenyl, $C_1$–$C_6$ alkylaryl, $C_1$–$C_6$ alkyl($C_3$–$C_{10}$)cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, or $C_1$–$C_6$ alkyl-morpholine;

with the proviso that at least one of Y or U is other than hydrogen or $C_1$–$C_4$ alkyl, and with the further proviso that at least one of $R^1$, $R^2$ or $R^3$ is other than hydrogen.

As used herein, the terms "Me", "Et", "Pr", "iPr", "Bu" and "t-Bu" refer to methyl, ethyl, propyl, isopropyl, butyl and tert-butyl, respectively.

As used herein, the terms "Halo", "Halide" or "Hal" refer to a chlorine, bromine, iodine or fluorine atom, unless otherwise specified herein.

As used herein the term "$C_1$–$C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1$–$C_6$ alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$C_1$–$C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$C_1$–$C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein the term "$C_1$–$C_6$ alkoxy" refers to a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

As used herein the term "$C_2$–$C_6$ alkenyl" refers to a straight or branched, monovalent, unsaturated aliphatic chain having from two to six carbon atoms. Typical $C_2$–$C_6$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

As used herein, the term "aryl" refers to monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

As used herein, the term "$C_1$–$C_6$ alkylaryl" refers to a straight or branched, monovalent, saturated aliphatic chain of 1 to 6 carbon atoms which has an aryl group attached to the aliphatic chain. Included within the term "$C_1$–$C_6$ alkylaryl" are the following:

and the like.

As used herein the term "($C_3$–$C_{10}$)cycloalkyl" refers to a saturated hydrocarbon ring structure containing from three to ten carbon atoms. Typical $C_3$–$C_{10}$ cycloalkyl groups include cyclopropyl, cyclobutyl, cyclopentyl, cyclohexyl, cycloheptyl, cyclooctyl, and the like. It is understood that "($C_3$–$C_8$)cycloalkyl" and "($C_4$–$C_6$)cycloalkyl" is included within the term "($C_3$–$C_{10}$)cycloalkyl".

As used herein, the term "$C_1$–$C_6$ alkyl($C_3$–$C_{10}$) cycloalkyl" refers to a straight or branched, monovalent, saturated aliphatic chain of 1 to 6 carbon atoms which has a ($C_3$–$C_{10}$)cycloalkyl attached to the aliphatic chain. Included within the term "$C_1$–$C_6$ alkyl($C_3$–$C_{10}$)cycloalkyl" are the following:

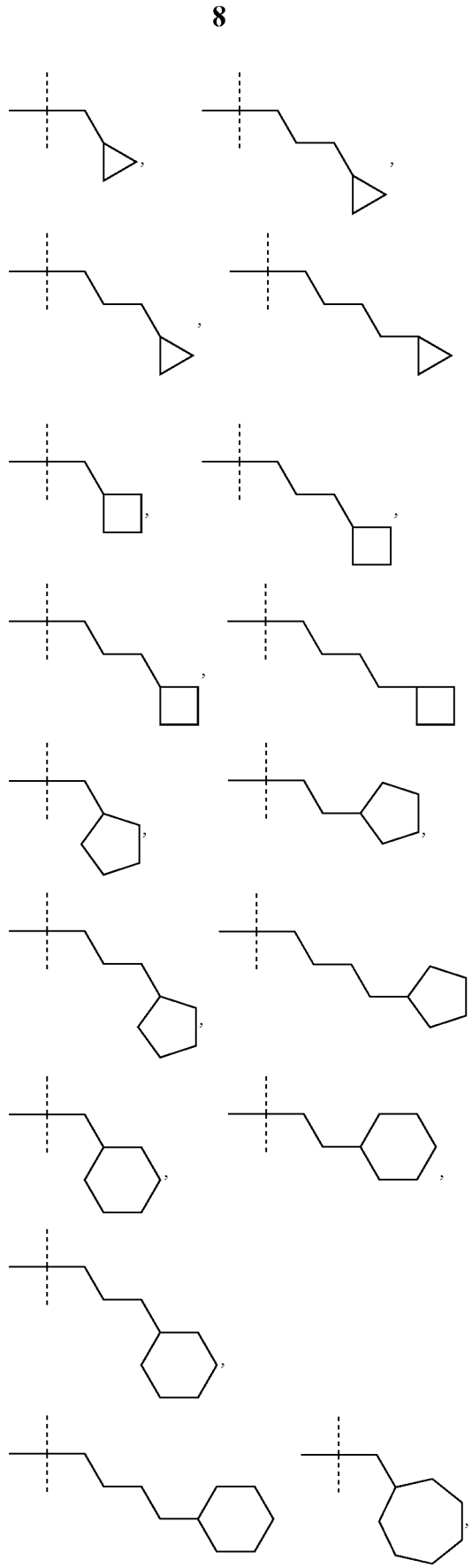

-continued

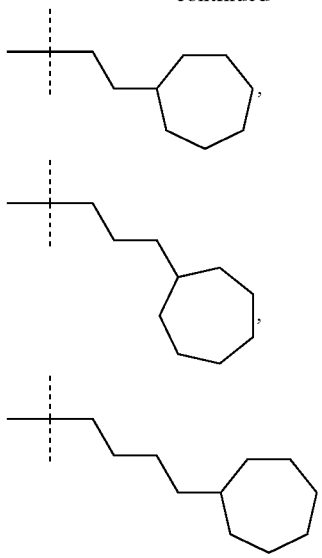

and the like.

As used herein the term "N,N-$C_1$-$C_6$ dialkylamine" refers to a nitrogen atom substituted with two straight or branched, monovalent, saturated aliphatic chains of 1 to 6 carbon atoms. Included within the term "N,N-$C_1$-$C_6$ dialkylamine" are —N(CH$_3$)$_2$, —N(CH$_2$CH$_3$)$_2$, —N(CH$_2$CH$_2$CH$_3$)$_2$, —N(CH$_2$CH$_2$CH$_2$CH$_3$)$_2$, and the like.

As used herein the term "$C_1$-$C_6$ alkyl-N,N-$C_1$-$C_6$ dialkylamine" refers to straight or branched, monovalent, saturated aliphatic chain of 1 to 6 carbon atoms which has an N,N-$C_1$-$C_6$ dialkylamine attached to the aliphatic chain. Included within the term "$C_1$-$C_6$ alkyl-N,N-$C_1$-$C_6$ dialkylamine" are the following:

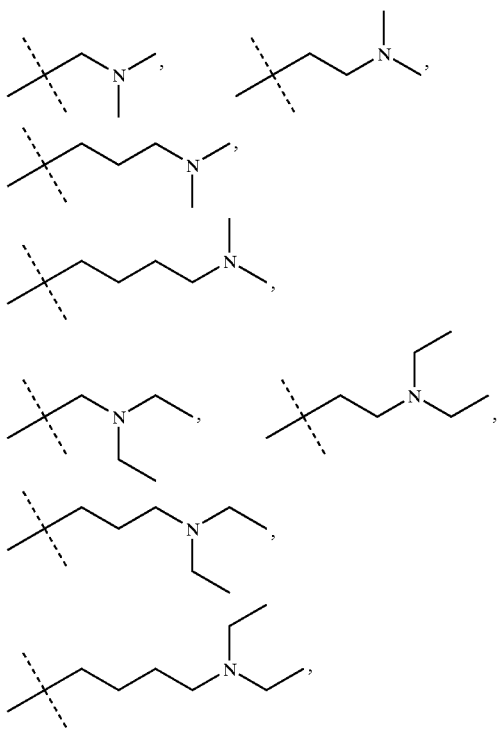

and the like.

As used herein the term "$C_1$-$C_6$ alkyl-pyrrolidine" refers to a straight or branched, monovalent, saturated aliphatic chain of 1 to 6 carbon atoms which has a pyrrolidine attached to the aliphatic chain. Included within the scope of the term "$C_1$-$C_6$ alkyl-pyrrolidine" are the following:

and the like.

As used herein the term "$C_1$-$C_6$ alkyl-piperidine" refers to a straight or branched, monovalent, saturated aliphatic chain of 1 to 6 carbon atoms which has a piperidine attached to the aliphatic chain. Included within the scope of the term "$C_1$-$C_6$ alkyl-piperidine" are the following:

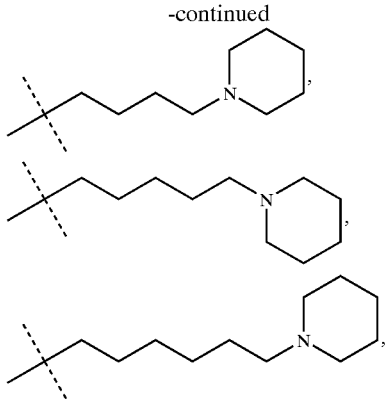

and the like.

As used herein the term "$C_1$–$C_6$ alkyl-morpholine" refers to a straight or branched, monovalent, saturated aliphatic chain of 1 to 6 carbon atoms which has a morpholine attached to the aliphatic chain. Included within the scope of the term "$C_1$–$C_6$ alkyl-morpholine" are the following:

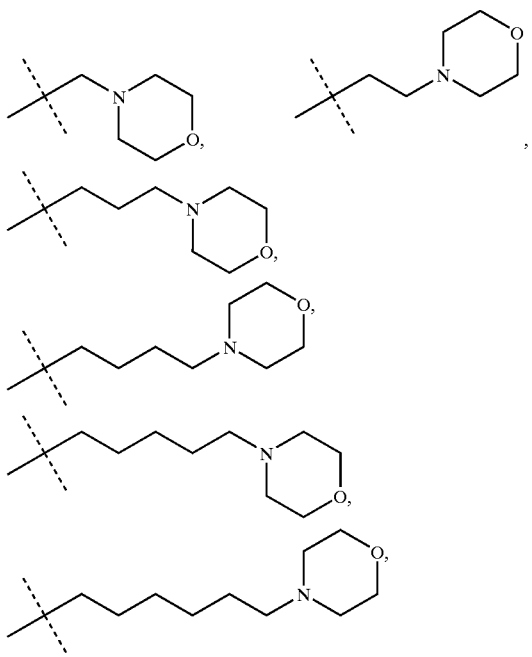

and the like.

The designation "◂▬■" refers to a bond that protrudes forward out of the plane of the page.

The designation "⋯⋯⋯" refers to a bond that protrudes backward out of the plane of the page.

As used herein the term "iGluR$_5$" refers to the kainate ionotropic glutamate receptor, subtype 5, of the larger class of excitatory amino acid receptors.

As used herein the term "migraine" refers a disorder of the nervous system characterized by recurrent attacks of head pain (which are not caused by a structural brain abnormality such as those resulting from tumor or stroke), gastrointestinal disturbances, and possibly neurological symptoms such as visual distortion. Characteristic headaches of migraine usually last one day and are commonly accompanied by nausea, emesis, and photophobia.

Migraine is a "chronic" condition. The term "chronic", as used herein, means a condition of slow progress and long continuance. As such, a chronic condition is treated when it is diagnosed and treatment is continued throughout the course of the disease. Conversely, the term "acute" means an exacerbated event or attack, of short course, followed by a period of remission. Thus, the treatment of migraine contemplates both acute events and chronic conditions. In an acute event, compound is administered at the onset of symptoms and discontinued when the symptoms disappear. As described above, a chronic condition is treated throughout the course of the disease.

It is understood that the term "selective iGluR$_5$ receptor antagonist" as used herein, includes those excitatory amino acid receptor antagonists which selectively bind to the iGluR$_5$ kainate receptor subtype, relative to the iGluR$_2$ AMPA receptor subtype. The selective iGluR$_5$ antagonist of formula I for use according to the method of the present invention has a binding affinity at least 20 fold greater for iGluR$_5$ than for iGluR$_2$.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science*, 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesultonate, ethanesulfonate, propanesulfonate, hydroxyethanesulfonate, naphthalene-1-sulfonate, napththalene-2-sulfonate, 1,5-naphthalenedisulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as, whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, i and conditions necessary to effect separation of the enantiomeric pair is well within the knowledge of one of ordinary skill in the art.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998.

For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein the term "Pg" refers to a suitable nitrogen protecting group. Examples of a suitable nitrogen protecting group as used herein refers to those groups intended to protect or block the nitrogen group against undesirable reactions during synthetic procedures. Choice of the suitable nitrogen protecting group used will depend upon the conditions that will be employed in subsequent reaction steps wherein protection is required, and is well within the knowledge of one of ordinary skill in the art. Commonly used nitrogen protecting groups are disclosed in Greene, "Protective Groups In Organic Synthesis," (John Wiley & Sons, New York (1981)). Suitable nitrogen protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, .alpha.-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha., .alpha.-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Preferred suitable nitrogen protecting groups are formyl, acetyl, methyloxycarbonyl, benzoyl, pivaloyl, t-butylacetyl, phenylsulfonyl, benzyl, t-butyloxycarbonyl (Boc) and benzyloxycarbonyl (Cbz).

Compounds of formula I can be prepared, for example, by following the procedures set forth in Scheme I. These schemes are not intended to limit the scope of the invention in any way. All substituents, unless otherwise indicated, are previously defined. The reagents and starting materials are readily available to one of ordinary skill in the art. For example, certain necessary starting materials can be prepared by one of ordinary skill in the art following procedures disclosed in U.S. Pat. No. 5,356,902, issued Oct. 18, 1994, *J. Org. Chem.,* 56(14), 4388 (1991), and *J. Org. Chem.,* 59, 7862 (1994).

include m-nitrobenzenesulfonyl chloride, p-nitrobenzenesulfonyl chloride, p-bromobenzenesulfonyl chloride, p-toluenesulfonyl chloride, benzenesulfonyl chloride, methanesulfonyl chloride, trifluoromethanesulfonyl chloride, and the like. The reaction mixture is stirred for about 5 to 20 hours at a temperature of about 0° C. to room temperature. The compound (2) is then isolated using standard procedures, such as extraction techniques. For example, the reaction mixture is washed with water, 1N aqueous HCl, saturated aqueous sodium bicarbonate, brine, dried over anhydrous sodium sulfate, filtered and concentrated to provide compound (2).

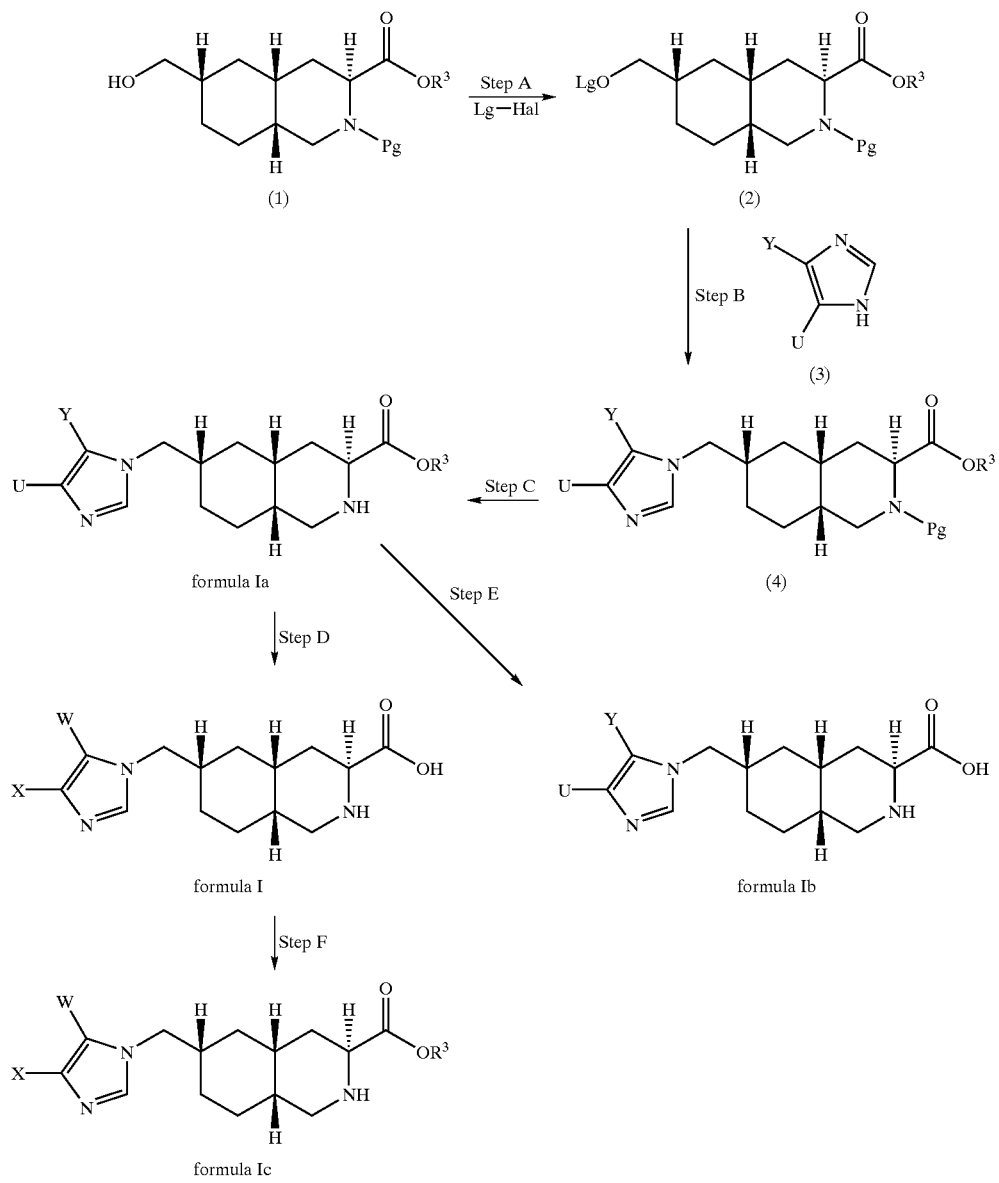

In Scheme I, step A, the compound of structure (1) is treated under standard conditions with a compound of formula Lg-Hal, wherein Lg is a suitable leaving group and Hal represents a chloro, bromo or iodo atom, to provide the compound of structure (2). For example, compound (1) is dissolved in a suitable organic solvent, such as methylene chloride and treated with about 1 to 2 equivalents of a compound of formula Lg-Hal and an excess of a suitable organic base, such as triethylamine. Examples of Lg-Hal In Scheme I, step B, compound (2) is non-regioselectively alkylated with the imidazole of structure (3) to provide the compound of structure (4). For example, compound (3) is dissolved in an organic solvent, such as N,N-dimethylformamide, under an atmosphere of nitrogen, and added to about 1 to 1.2 equivalents of a base in N,N- dimethylformamide. The reaction mixture is then treated with compound (2) dissolved in N,N-dimethylformamide and the reaction is stirred at room temperature for about 10 to 20 hours. The reaction is then quenched and compound (4) is isolated and purified by standard techniques well known in the art. For example, the reaction is quenched with saturated aqueous sodium bicarbonate and the quenched reaction mixture is filtered. The filtrate is extracted with a suitable organic solvent, such as ethyl acetate, the organic extracts are combined, washed with brine, dried over anhydrous magnesium sulfate, filtered and concentrated to provide crude compound (4). This crude material is then purified by chromatography on silica gel with a suitable eluent, such as ethyl acetate or methanol/chloroform to provide purified compound (4).

Alternatively, in Scheme I, step B, compound (2) is regioselectively alkylated with the imidazole of structure (3a):

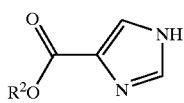

(3a)

to provide predominately the compound of structure (4a):

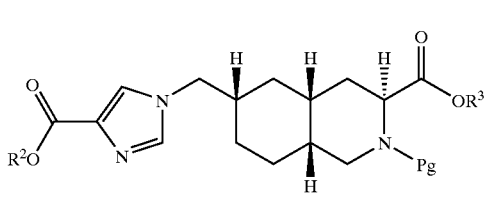

(4a)

as opposed to the compound of (4b):

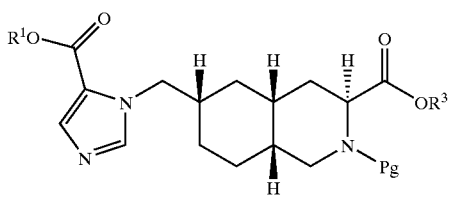

(4b)

For example, compound (3a) is combined with a suitable base in a suitable organic solvent, at a temperature of about 0° C. to about 40° C. with about 20° C. being preferred. Examples of suitable organic solvents include tetrahydrofuran, 1,4-dioxane, diethyl ether, glymes, and the like, with tetrahydrofuran being preferred. Examples of suitable bases include sodium hydride, DBU, potassium carbonate, potassium tert-butoxide, and the like, with sodium hydride being preferred. The reaction mixture is stirred for about 0.5 hours to about 1.5 hours, with about 1 hour being preferred. This reaction mixture is then combined with a compound of structure (2) as defined above, at a temperature of about 0° C. to about 40° C. with about 20° C. being preferred. The reaction mixture is allowed to stir for about 4 hours to about 40 hours with about 16 hours being preferred. The reaction is then quenched and compound (4a) is isolated and purified by standard techniques well known in the art. For example, the reaction is quenched with water and extracted with a suitable solvent, such as methylene chloride. The organic extracts are dried over anhydrous sodium sulfate, filtered, and concentrated under vacuum to provide crude (4a). This crude material is then purified by flash chromatography on silica gel with a suitable eluent, such as 5% to 10% ethanol/toluene containing 0.5% dimethylamine to provide purified compound of structure (4a).

In Scheme I, step C, compound (4) is deprotected under standard conditions well known in the art to provide the compound of formula Ia. For example, when Pg is a methoxycarbonyl protecting group, compound (4) is dissolved in a suitable organic solvent, such as dry dichloromethane under an atmosphere of nitrogen, and treated with trimethylsilyl iodide at room temperature. The reaction mixture is stirred for about 10 to 20 hours. The reaction is quenched and compound of formula Ia is isolated and purified using standard techniques well to known to one of ordinary skill in the art. For example, the reaction is quenched by addition of ethanol and then concentrated under vacuum. The residue is dissolved in a suitable organic solvent, such as ethyl acetate and the organic is rinsed with saturated sodium bicarbonate. The aqueous layer is extracted with ethyl acetate. The organic extracts and organic layer are combined, washed with brine, dried over anhydrous sodium sulfate, filtered, and concentrated under vacuum to provide crude compound of formula Ia. This crude material is then purified by chromatography on silica gel with a suitable eluent, such as methanol/chloroform to provide purified compound of formula Ia.

In Scheme I, step D, the compound of formula Ia is hydrolyzed to the compound of formula I under conditions well known in the art. For example, compound of formula Ia is dissolved in a suitable organic solvent, such as methanol, and treated with an excess of a suitable base. Examples of suitable bases include aqueous lithium hydroxide, sodium hydroxide, potassium hydroxide, and the like. Lithium hydroxide is preferred. The reaction is stirred for about 10 to 20 hours. The reaction mixture is then neutralized to pH 6 with 1 N HCl and concentrated under vacuum to provide crude compound of formula I. This crude material is then purified by techniques well known in the art, such as cation exchange chromatography eluting with methanol/water followed by ammonium hydroxide/methanol to provide purified compound of formula I.

In Scheme I, step E, the compound of formula Ia is selectively hydrolyzed to provide the compound of formula Ib. For example, the compound of formula Ia is dissolved in 5 N aqueous HCl and heated at about 50° C. for about 3 hours. It is then allowed to stir at room temperature for about 18 hours and the reaction is concentrated under vacuum to provide crude compound of formula Ia. This crude material is purified by standard techniques well known to one of ordinary skill, for example by reverse phase chromatography on C18 modified silica gel with a suitable eluent, such as acetonitrile in aqueous 0.1% HCl to provide purified compound of formula Ib.

In Scheme I, step f, the compound of formula I is selectively esterified to provide the compound of formula Ic. For example, the compound of formula I is dissolved in a suitable organic solvent, such as ethanol and the solution is treated with 1M HCl in diethyl ether. The reaction is heated at reflux for about 8 to 12 hours, cooled, and concentrated under vacuum to provide crude compound of formula Ic. This crude material is then purified by standard techniques well known in the art, for example by reverse phase chromatography on C18 modified silica gel with a suitable eluent, such as acetonitrile in aqueous 0.1% HCl to provide purified compound of formula Ic.

The following examples further illustrate the invention and represent typical syntheses of the compounds of formula I as described generally above. The reagents and starting materials are readily available to one of ordinary skill in the art. As used herein, the following terms have the meanings indicated: "eq" or "equiv." refers to equivalents; "g" refers to grams; "mg" refers to milligrams; "L" refers to liters; "mL" refers to milliliters; "μL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to parts per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "aq" refers to aqueous; "EtOAc" refers to ethyl acetate; "iPrOAc" refers to isopropyl acetate; "MeOH" refers to methanol; "EtOH" refers to ethanol; "MTBE" refers to tert-butyl methyl ether, "tlc" refers to thin layer chromatography; and "RT" refers to room temperature.

Preparation 1

Preparation of [3S,4aR,6S,8aR]-6-methylidine-2-(methoxycarbonyl)-1,2,3,4,4a,5,6,7,8,8a-decahydroisoguinoline-3-carboxylic Acid.

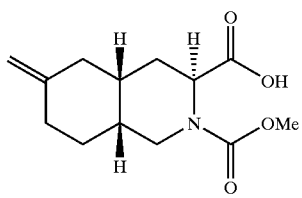

A slurry of methyltriphenylphosphonium bromide (12.4 g, 34.6 mmol) in THF (25 mL) was cooled to −10 to −12° C. under an atmosphere of nitrogen and treated with sodium hexamethyidisilazide (35 mL of a 1 M solution in THF) via syringe over 6 to 8 minutes with stirring. The reaction mixture was then stirred for 20 minutes at −10 to −12° C. and added via cannula over 3–4 minutes to [3S,4aR,6S,8aR]-6-oxo-2-(methoxycarbonyl)-1,2,3,4,4a,5,6,7,8,8a-decahydroisoquinoline-3-carboxylic acid (10.0 g, 26.6 mmol), [which had previously been treated with sodium hexamethyidisilazide (27 mL of 1 M solution in THF) at 0–3° C. and stirred for 10 minutes] dissolved in DMF (20 mL) and cooled to 0–3° C. under an atmosphere of nitrogen. This was followed by a THF (3 mL) rinse of the flask holding the Wittig reagent which was also added to the reaction mixture. The reaction mixture was then allowed to stir for 5 minutes at 0–3° C., was then allowed to warm to room temperature, and stirred for an additional 3 hours. Ethyl acetate (100 mL) and water (50 mL) were added with stirring and then the layers were separated. The organic layer was extracted with water (50 mL) and the combined aqueous portions were washed with methylene chloride (5×75 mL). The aqueous was then treated with 6M HCl (15 mL) and extracted with methylene chloride (3×50 mL). The organic extracts were dried over anhydrous sodium sulfate, filtered, and concentrated under vacuum to provide the title compound (6.59 g, 98%) as a yellow oil.

Alternative Synthesis of [3S,4aR,6S,8aR]-6-methylidine-2-(methoxycarbonyl)-1,2,3,4,4a,5,6,7,8,8a-decahydroisoguinoline-3-carboxylic Acid.

A slurry of [3S,4aR,6S,8aR]-6-oxo-2-(methoxycarbonyl)-1,2,3,4,4a,5,6,7,8,8a-decahydroisoquinoline-3-carboxylic acid (50.0 g, 0.133 mol, 1.0 equiv) and methyltriphenylphosphonium bromide (66.4 g, 0.186 mol, 1.4 equiv) in THF (150 mL) and DMF (25 mL) was stirred mechanically under an atmosphere of nitrogen and cooled to −10° C. Potassium tert-butoxide solution (187 mL of 1.7 M in THF, 0.319 mol, 2.4 equiv) was added dropwise over a 10 minute period. A mild exotherm throughout this addition resulted in an increase of the reaction temperature to 6° C. The slurry was allowed to warm to room temperature and stirred thus for 2.5 hours (complete by TLC at this time). Reaction was partitioned between water (250 mL) and EtOAc (250 mL) and the layers were separated. The organic phase was extracted with water (2×100 mL) and the aqueous portions were combined and washed with dichloromethane (5×300 mL). The aqueous solution was made acidic by addition of 6 M HCl solution (50 mL) and extracted with dichloromethane (3×150 mL). These last three organic extracts were combined, dried with sodium sulfate and concentrated under reduced pressure to provide the title compound as a yellow film (36.17 g). Estimated potency of the product by proton NMR was 89 wt % (remainder residual solvents) for a corrected yield of 32.2 g (95.6%).

Preparation 2

Preparation of [3S,4aR,6S,8aR]-Ethyl-6-methylidine-2-(methoxycarbonyl)-1,2,3,4,4a,5,6,7,8,8a-decahydroisoquinoline-3-carboxylate.

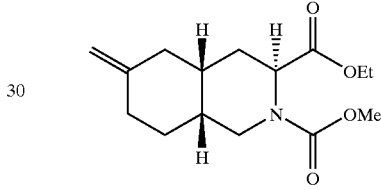

[3S,4aR,6S,8aR]-6-methylidine-2-(methoxycarbonyl)-1,2,3,4,4a,5,6,7,8,8a-decahydroisoquinoline-3-carboxylic acid (6.59 g, 26.0 mmol, prepared in preparation 1) was dissolved in acetonitrile (26 mL) and treated with triethylamine (7.25 mL, 52 mmol) and bromoethane (5.82 mL, 78 mmol). The reaction was heated at 50° C. for about 3 hours, cooled and partitioned between 50:50 ethyl acetate/heptane (100 ml) and 1N HCl (75 mL). The organic phase was isolated and washed with water (3×30 mL), saturated sodium bicarbonate (30 mL), brine (30 mL), dried over anhydrous sodium sulfate, filtered, and concentrated under vacuum to provide the crude title compound as an amber oil. This crude material was dissolved in 10% ethyl acetate/heptane (15 mL) and applied to a plug of silica gel (10 g in 10% ethyl acetate/heptane). The plug was eluted with 10% ethyl acetate/heptane (10 mL), 15% ethyl acetate/heptane (15 mL), and 25% ethyl acetate/heptane (90 mL). The eluents were combined and concentrated under vacuum to provide the purified titled compound (6.84 g, 91%) as a colorless oil.

Preparation 3

Preparation of [3S,4aR,6S,8aR]-Ethyl-6-(hydroxymethyl)-2-(methoxycarbonyl)-1,2,3,4,4a,5,6,7,8,8a-decahydroisoquinoline-3-carboxylate.

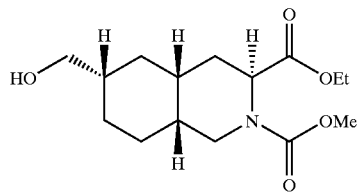

[3S,4aR,6S,8aR]-Ethyl-6-methylidine-2-(methoxycarbonyl)-1,2,3,4,4a,5,6,7,8,8a-decahydroisoquinoline-3-carboxylate (51.1 g, 181 mmol, prepared in preparation 2) was dissolved in THF (250 mL) and cooled to about −15° C. under an atmosphere of nitrogen with stirring. A 1M solution of BH₃·THF (121 mL, 121 mmol, in THF) was added dropwise over 5–7 minutes and the reaction mixture was stirred for about 2 hours at −10 to −12° C. The reaction was then slowly treated with ethanol (32 mL, exotherm) over 7–9 minutes and then treated slowly with 30% H₂O₂ (91 mL, exotherm) over 15 minutes. The reaction mixture was allowed to warm to room temperature over 45 minutes and then partitioned between ethyl acetate (450 mL) and 50% saturated sodium chloride solution (700 mL). The aqueous layer was extracted with ethyl acetate (250 mL) and the combined organics were washed with 5% sodium bisulfite solution (400 mL), brine (200 mL), dried over anhydrous sodium sulfate, filtered, and concentrated under vacuum to provide the title compound (54.41 g) as a colorless oil.

EXAMPLE 1

Preparation of [3S,4aR,6S 8aR]-Ethyl-6-((4-ethoxycarbonyl-5-methyl-1H-imidazol-1-yl)methyl)-1,2,3,4,4a,5,6,7,8,8a-decahydroisoquinoline-3-carboxylate.

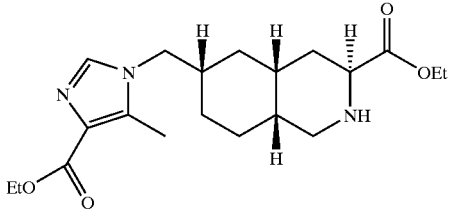

Preparation of [3S,4aR,6S,8aR]-Ethyl-6-((3-nitrophenylsulfonyloxy)methyl)-2-(methoxycarbonyl)-1,2,3,4,4a,5,6,7,8,8a-decahydroisoguinoline-3-carboxylate.

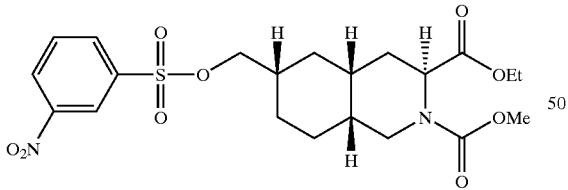

Scheme I, step A: To a solution of 1.0 g of [3S,4aR,6S, 8aR]-ethyl-6-(hydroxymethyl)-2-(methoxycarbonyl)-1,2,3,4,4a,5,6,7,8,8a-decahydroisoquinoline-3-carboxylate and 0.78 g of 3-nitrobenzenesulphonyl chloride in 25 ml methylene chloride at 5° C. was added 1.4 ml of triethylamine dropwise. The reaction was allowed to warm to room temperature and stirred for 18 h. The crude reaction solution was washed with water, 1N hydrochloric acid, saturated aqueous sodium bicarbonate and brine, dried (sodium sulfate), filtered and evaporated. The resulting viscous oil was dried under vacuum at 50° C. to provide 1.1 g of the intermediate title compound: MS m/z 486 (m⁺+1);

400-MHz ¹H NMR (CDCl₃) δ 1.15 (m, 2H), 1.2 (t, 3H), 1.4–1.6 (m, 5H), 1.85 (m, 3H), 2.1 (m, 1H), 3.25 (m, 1H), 3.35 (dd, 1H), 3.65 (s, 3H), 3.95 (m, 2H), 4.15 (q, 2H), 4.35 (t, 1H), 7.75 (t, 1H), 8.2 (d, 1H), 8.5 (d, 1H), 8.7 (s, 1H).

Preparation of [3S,4aR,6S,8aR]-Ethyl-6-((4-ethoxycarbonyl-5-methyl-1H-imidazol-1-yl)methyl)-2-(methoxycarbonyl)-1,2,3,4,4a,5,6,7,8,8a-decahydroisoquinoline-3-carboxylate.

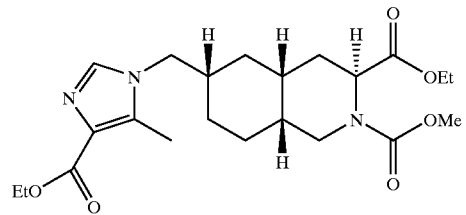

Scheme I, step B: Sodium hydride (0.24 g, 1.2 eq) was washed with hexanes (3×10 ml) and suspended in dry THF (10 ml). To this was added a solution of 0.848 g of ethyl 4-methyl-5-imidazolecarboxylate in THF (5 ml) dropwise. The reaction mixture was stirred at 20° C. for 1.5 h and DMF (10 ml) was added. To the resulting solution was slowly added a solution of 2.43 g of [3S,4aR,6S,8aR]-ethyl-6-((3-nitrophenylsulfonyloxy)methyl)-2-(methoxycarbonyl)-1,2,3,4,4a,5,6,7,8,8a-decahydroisoquinoline-3-carboxylate in THF (10 ml). The reaction was stirred at ambient temperature over night under N₂. The reaction was quenched with saturated aqueous sodium bicarbonate. The resulting white solid was removed by filtration and the filtrate was extracted with ethyl acetate (3×10 ml). The combined organic extract was washed with brine, dried (MgSO₄), filtered, and evaporated to a light brown oil. The crude product was chromatographed over silica gel eluting with ethyl acetate to give 1.09 g of the intermediate title compound: MS m/z: 456.3 (m⁺+1);

400-MHz ¹H NMR (CDCl₃) δ 7.62 (s, 1H), 4.42–4.33 (m, 3H), 4.20–4.16 (m, 2H), 3.84–3.72 (m, 2H), 3.70 (s, 3H), 3.48–3.42 (dd, 2H), 3.40–3.28 (t, 1 H), 2.50 (s, 3 H), 2.24–2.16 (m, 1H), 1.95–1.88 (m, 1H), 1.86–1.80 (m, 2H), 1.80–1.75 (m, 1H), 1.67–1.60 (m, 2H), 1.56–1.43 (m, 2H), 1.42–1.36 (t, 3H), 1.26–1.22 (t, 3H), 1.20–1.08 (m, 2H).

Preparation of [3S,4aR,6S,8aR]-Ethyl-6-((4-ethoxycarbonyl-5-methyl-1H-imidazol-1-yl)methyl)-1,2,3,4,4a,5,6,7,8 8a-decahydroisoguinoline-3-carboxylate.

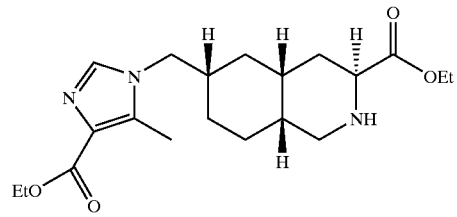

Scheme I, step C: To a solution of 0.435 g of [3S,4aR,6S,8aR]-ethyl-6-((4-ethoxycarbonyl-5-methyl-1H-imidazol-1-yl)methyl)-2-(methoxycarbonyl)-1,2,3,4,4a,5,6,7,8,8a-decahydroisoquinoline-3-carboxylate in dry dichloromethane (30 ml) at 20° C. was added 0.71 ml of trimethylsilyl iodide dropwise under N₂. The reaction was stirred at 20° C. for 18 h. The reaction was quenched by addition of EtOH (5 ml) and concentrated to dryness. The residue was dissolved in ethyl acetate and saturated aqueous sodium bicarbonate. The two phases were separated. The aqueous layer was extracted with EtOAc (3×10 ml). The combined organic extracts were washed with brine, dried (sodium sulfate), filtered, and evaporated. The resulting residue chromatographed over silica gel eluting with 1% methanol in chloroform to give 0.205 g of the intermediate title compound: MS m/z: 378.3 (m$^+$+1);
400-MHz $^1$H NMR (CDCl$_3$) δ 7.39 (s, 1H), 7.25 (s, 1 H), 4.37–4.32 (q, 2H), 4.19–4.13 (q, 2H), 3.74–3.72 (m, 3H), 3.49–3.426(dd, 1H), 3.40–3.28 (t, 1H), 2.90–2.75 (dd, 1H), 2.52 (s, 3H), 2.19–2.09 (m, 3H), 1.92–1.88 (m, 2H), 1.75–1.72 (m, 2H), 1.63–1.59 (m, 1 H), 1.48–1.59 (m, 1H), 1.44–1.36 (t, 3H), 1.27–1.23 (t, 3H), 1.03–0.88 (m, 2H).

Preparation of [3S,4aR,6S,8aR]-Ethyl-6-((4-ethoxycarbonyl-5-methyl-1H-imidazol-1-yl)methyl)-1,2,3,4,4a,5,6,7,8,8a-decahydroisoquinoline-3-carboxylate dihydrochloride.

To a solution of 0.325 g of [3S,4aR,6S,8aR]-ethyl-6-((4-ethoxycarbonyl-5-methyl-1H-imidazol-1-yl)methyl)-1,2,3,4,4a,5,6,7,8,8a-decahydroisoquinoline-3-carboxylate in dry ethyl acetate (5 mL) at 20° C. was added 3.4 ml of a 1.0M solution of HCl in diethyl ether. The resulting precipitate was collected through filtration and vacuum dried at 50° C. to yield 0.214 g of the final title compound, [3S,4aR,6S,8aR]-ethyl-6-((4-ethoxycarbonyl-5-methyl-1H-imidazol-1-yl)methyl)-1,2,3,4,4a,5,6,7,8,8a-decahydroisoquinoline-3-carboxylate dihydrochloride: MS m/z: 378.3 (m$^+$+1-HCl);
$^1$H NMR 400 MHz (CD$_3$OD) δ 9.12 (s, 1 H), 4.44–4.38 (m, 2H), 4.27–4.22 (m, 2H), 4.16–4.09 (m, 3H), 3.38–3.32 (t, 1 H), 3.06 (br s, 2 H), 3.08–3.02 (dd, 1H), 2.62 (s, 3H), 2.17–2.02 (m, 2H), 1.98–1.90 (m, 3H), 1.74–1.64 (m, 2H), 1.63–1.59 (m, 1H), 1.46–1.33 (m, 5H), 1.31–1.25 (t, 3H), 1.23–1.08 (m, 1H).

EXAMPLE 2

Preparation of [3S,4aR,6S,8aR]-6-((4-carboxylic Acid-5-methyl-1H-imidazol-1-yl)methyl)-1,2,3,4,4a,5,6,7,8,8a-cecahydroisoquinoline-3-carboxylic Acid.

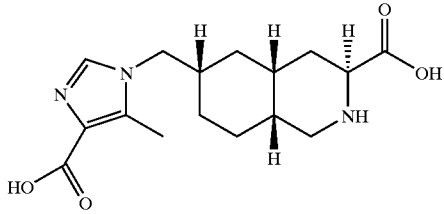

Scheme I, step D: To a solution of 0.267 g of [3S,4aR,6S,8aR]-ethyl-6-((4-ethoxycarbonyl-5-methyl-1H-imidazol-1-yl)methyl)-1,2,3,4,4a,5,6,7,8,8a-decahydroisoquinoline-3-carboxylate in methanol at 20° C. was added 7.1 ml of a 1.0 M aqueous solution of lithium hydroxide. The resulting mixture was stirred for 18 h. Upon completion, the reaction was neutralized to pH=6 with 1.0N HCl and evaporated to a white solid. The crude product was purified by strong cation exchange chromatography eluting with 50% methanol in water followed by 2.0M ammonium hydroxide in methanol to provide 0.226 g of the title compound: MS m/z: 322.2 (m$^+$+1);
400-MHz $^1$H NMR (CD$_3$OD) δ 7.60 (br s, 1 H), 3.94–3.82 (m, 2H), 3.79–3.73(d, 1H), 3.32–3.24 (d, 1H), 3.22–3.18 (t, 1H), 2.89–2.82 (d, 1H), 2.50 (m, 3H), 2.18–2.01 (m, 2H), 1.96–1.90 (m, 1 H), 1.86–1.73 (m, 2H), 1.70–1.62 (br. s, 2H), 1.58–1.42 (m, 1 H), 1.42–1.30 (br. s, 2H), 1.03–0.88 (m, 1 H) (note that the two COOH and one NH protons were exchanged with the solvent).

Preparation of [3S,4aR,6S,8aR]-6-((4-Carboxylic Acid-5-methyl-1H-imidazol-1-yl)methyl)-1,2,3,4,4a,5,6,7,8,8a-decahydroisoquinoline-3-carboxylic Acid dihydrochloride.

To a solution of 0.223 g of [3S,4aR,6S,8aR]-6-((4-carboxylic acid-5-methyl-1H-imidazol-1-yl)methyl)-1,2,3,4,4a,5,6,7,8,8a-decahydroisoquinoline-3-carboxylic acid in dry ethyl acetate (5 mL) at 20° C. was added 2.1 ml of a 1.0M solution of HCl in diethyl ether. The resulting precipitate was collected through filtration and vacuum dried at 50° C. to yield 0.21 g of [3S,4aR,6S,8aR]-6-((4-carboxylic acid-5-methyl-1H-imidazol-1-yl)methyl)-1,2,3,4,4a,5,6,7,8,8a-decahydroisoquinoline-3-carboxylic acid dihydrochloride: MS m/z: 322.4 (m$^+$+1-HCl).
400-MHz $^1$H NMR (D$_2$O) δ 0.90 (m, 1H), 1.15 (m, 3H), 1.40 (m, 2H), 1.62–1.95 (m, 4H), 2.25 (3H), 2.85 (dd, 1 H), 2.98 (t, 1 H), 3.55 (dd, 1 H), 3.82 (d, 2H), 4.20 (q, 1H), 8.5 (s, 1H).

EXAMPLE 3

Preparation of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate.

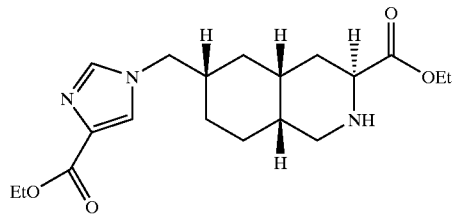

Preparation of [3S,4aR,6S,8aR]-Ethyl-6-((4-ethoxycarbonyl-1H-imidazol-1-yl)methyl)-2-(methoxycarbonyl)-1,2,3,4,4a,5,6,7,8,8a-decahydroisoquinoline-3-carboxylate.

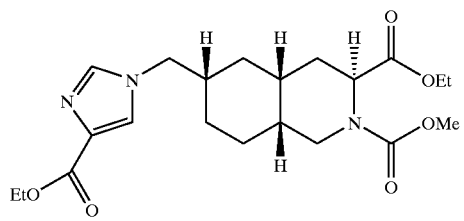

Scheme I, step B: In 100 mL anhydrous dimethylformamide was dissolved 6.81 g of ethyl-4-imidazolecarboxylate. At room temperature, 1.94 g of NaH were added and the reaction was allowed to stir for 1 hour. To the reaction was added 23.56 g of [3S,4aR,6S,8aR]-ethyl-6-((3-nitrophenylsulfonyloxy)methyl)-2-(methoxycarbonyl)-1,2,3,4,4a,5,6,7,8,8a-decahydroisoquinoline-3-carboxylate dissolved in 100 mL dimethylformamide. The reaction mixture was stirred at ambient temperature overnight and evaporated to dryness. The residue was redissolved in ethyl acetate and washed with saturated sodium bicarbonate solution. The layers were separated and the aqueous was extracted with three portions of ethyl acetate. The combined organic extracts were washed with brine, dried over sodium sulfate, filtered, and concentrated in vacuo. The resulting residue was chromatographed over silica gel eluting with 0% to 2% methanol in chloroform to give 8.04 g of the intermediate title compound: MS m/z: 422.1 (m$^+$+1);
$^1$H NMR (400 MHz, CDCl$_3$) δ 7.53 (s, 1 H), 7.4 (s, 1 H), 4.39–4.3 (m, 3H), 4.2–4.1 (m, 2H), 3.85–3.75 (m, 2H), 3.7

(s, 3H), 3.42–3.38 (dd, 1 H), 3.35–3.25 (t, 1 H), 2.2–2.1 (m, 1H), 1.95–1.9 (m, 1H), 1.89–1.75 (m, 2H), 1.7–1.65 (m, 1H), 1.64–1.55 (m, 1 H), 1.54–1.4 (m, 3H), 1.38–1.3 (t, 3H), 1.25–1.2 (t, 3H), 1.2–1.0 (m, 2H).

Alternative Preparation of [3S,4aR,6S,8aR]-Ethyl-6-((4-ethoxycarbonyl-1H-imidazol-1-yl)methyl)-2-(methoxycarbonyl)-1,2,3,4,4a,5,6,7,8,8a-decahydroisoquinoline-3-carboxylate.

Scheme I, step B: Ethyl-4-imidazolecarboxylate (486 mg, 3.46 mmol) was added in portions to a slurry of sodium hydride (146 mg of a 60% mineral oil dispersion, 3.64 mmol) in THF (3.0 mL). The resulting tea-colored solution was stirred at room temperature for 55 minutes. It was then treated with [3S,4aR,6S,8aR]-ethyl-6-((3-nitrophenylsulfonyloxy)methyl)-2-(methoxycarbonyl)-1,2,3,4,4a,5,6,7,8,8a-decahydroisoquinoline-3-carboxylate (1.68 g, 3.46 mmol, prepared in example 1) dissolved in THF (3.5 mL), and the reaction mixture was stirred overnight at room temperature. The reaction was then partitioned between dichloromethane (6.5 mL) and water (6.5 mL), and the layers were separated. The aqueous layer was extracted with dichloromethane (5 mL). The organic extract and organic layer were combined, dried over anhydrous sodium sulfate, filtered, and concentrated under vacuum to provide the crude title compound. This material was purified flash chromatography (5% to 10% ethanol/toluene containing 0.5% dimethylamine, 34 g silica gel) to provide the purified intermediate title compound (1.16 g, 79%) as a colorless film.

Preparation of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate.

Scheme I, step C: To a solution of 0.90 g of [3S,4aR,6S,8aR]-ethyl-6-((4-ethoxycarbonyl-1H-imidazol-1-yl)methyl)-2-(methoxycarbonyl)-1,2,3,4,4a,5,6,7,8,8a-decahydroisoquinoline-3-carboxylate in 20 ml of methylene chloride was added 1.5 ml trimethylsilyl iodide. The reaction was stirred at room temperature for six hours, quenched with excess absolute ethanol and evaporated to dryness. The residue was purified by strong cation exchange chromatography eluting with 10–50% methanol in chloroform followed by 50% 2M ammonia/methanol in chloroform to provide the final title compound, [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate.

Preparation of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate dihydrochloride.

[3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate was dissolved in ethyl acetate and excess 1M HCl in diethyl ether was added. The resulting white precipitate was filtered and vacuum dried at 50° C. for 18 hr to give 0.62 g of [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate dihydrochloride: MS m/z: 364 (m$^+$+1); Analysis calculated for $C_{19}H_{29}N_3O_4 \cdot 2HCl \cdot H_2O$: C, 50.20; H, 6.89; N, 9.25. Found: C, 50.51; H, 6.86; N, 9.25.

Preparation of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate Citrate (1:1 Molar Salt Complex).

[3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate (511 mg, 1.04 mmol) was dissolved in 2-propanol (3.0 mL) and treated with a solution of citric acid (270 mg, 1.04 mmol, dissolved in 2.0 mL 2-propanol). The resulting slurry was heated to effect solution and seeded with authentic salt. The mixture was cooled slowly to room temperature with stirring and then cooled further in an ice-water bath. [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate citrate was collected by filtration as a colorless crystalline solid (717 mg, 92%).

Preparation of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate Methanesulfonate.

The methanesulfonic acid salt of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate is prepared in a manner analogous to the procedures described above from one equivalent of methanesulfonic acid and one equivalent of [3S,4aR,6S,8aR]-Ethyl-6-((4-ethoxycarbonyl-1H-imidazol-1-yl)methyl)-1,2,3,4,4a,5,6,7,8,8a-decahydroisoquinoline-3-carboxylate in ethyl acetate.

EXAMPLE 4

Preparation of [3S,4aR,6S,8aR]-6-((4-Carboxylic Acid-1H-imidazol-1-yl)methyl)-1,2,3,4,4a,5,6,7,8,8a-decahydroisoquinoline-3-carboxylic Acid Dihydrochloride.

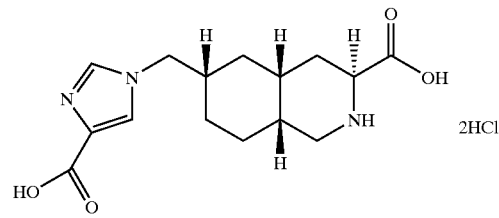

Scheme I, step D: A solution of 0.80 g of [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate (prepared in example 3) in 10 mL of 5N HCl was heated at 70° C. for 18 h. After cooling to 20° C., the solution was evaporated and the resulting residue vacuum dried at 50° C. to give 0.526 g of the title compound: MS m/z: 308 (m$^+$+1); Analysis calculated for $C_{15}H_{21}N_3O_4 \cdot 2HCl \cdot H_2O$: C, 45.2; H, 6.34; N, 10.54. Found: C, 45.72; H, 6.30; N, 10.75.

EXAMPLE 5

Preparation of [3S,4aR,6S,8aR]-Ethyl-6-((5-ethoxycarbonyl-1H-imidazol-1-yl)methyl)-1,2,3,4,4a,5,6,7,8,8a-decahydroisoquinoline-3-carboxylate Dihydrochloride.

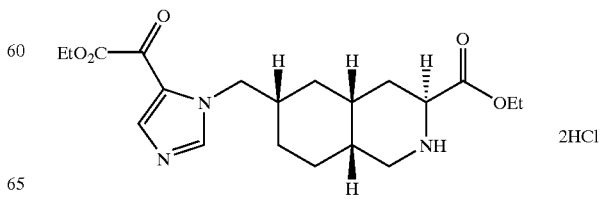

Preparation of [3S,4aR,6S,8aR]-Ethyl-6-((5-ethoxycarbonyl-1H-imidazol-1-yl)methyl)-2-(methoxycarbonyl)-1,2,3,4,4a,5,6,7,8,8a-decahydroisoquinoline-3-carboxylate.

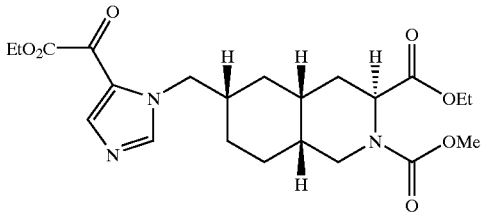

Scheme I, step B: Following the identical procedure set forth in example 3, chromatographic separation provided 0.76 g of the title compound: MS m/z: 422.2 (m$^+$+1); 400 MHz $^1$H NMR (CDCl$_3$) δ 7.8–7.7 (bs, 1 H), 7.7–7.65 (bs, 1 H), 4.35–4.3 (t, 1 H), 4.3–4.2 (m, 2H), 4.2–4.1 (m, 4H), 3.7–3.6 (s, 3H), 3.45–3.35 (dd, 1 H), 3.3–3.2 (t, 1H), 2.2–2.1 (m, 1H), 1.95–1.85 (m, 3H), 1.7–1.6 (m, 1H), 1.6–1.5 (m, 1H), 1.5–1.35 (m, 3H), 1.35–1.3 (t, 3H), 1.25–1.2 (t, 3H), 1.2–1.05 (m, 2H).
Preparation of Final Title Compound.

Scheme I, step C: In a manner analogous to the procedure described in example 3, [3S,4aR,6S,8aR]-ethyl-6-((5-ethoxycarbonyl-1H-imidazol-1-yl)methyl)-1,2,3,4,4a,5,6,7,8,8a-decahydroisoquinoline-3-carboxylate dihydrochloride was obtained from [3S,4aR,6S,8aR]-ethyl-6-((5-ethoxycarbonyl-1H-imidazol-1-yl)methyl)-2-(methoxycarbonyl)-1,2,3,4,4a,5,6,7,8,8a-decahydroisoquinoline-3-carboxylate: MS m/z: 364(m$^+$+1); Analysis calculated for C$_{19}$H$_{29}$N$_3$O$_4$.2HCl H$_2$O: C, 50.20; H, 6.89; N, 9.25. Found: C, 50.43; H, 7.17; N, 9.12.

EXAMPLE 6

Preparation of [3S,4aR,6S,8aR]-6-((5-Carboxylic Acid-1H-imidazol-1-yl)methyl)-1,2,3,4,4a,5,6,7,8,8a-decahydroisoquinoline-3-carboxylic Acid Dihydrochloride.

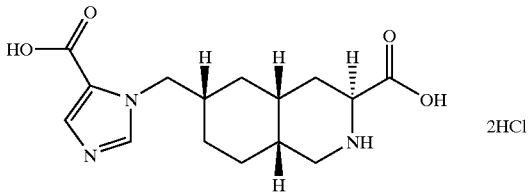

Scheme I, step D: In a manner analogous to the procedure described in example 4, the title compound was obtained from [3S,4aR,6S,8aR]-ethyl-6-((5-ethoxycarbonyl-1H-imidazol-1-yl)methyl)-1,2,3,4,4a,5,6,7,8,8a-decahydroisoquinoline-3-carboxylate dihydrochloride (prepared in example 5): MS m/z: 308.1 (m$^+$+1); Analysis calculated for C$_{15}$H$_{21}$N$_3$O$_4$.2HCl H$_2$O: C, 45.2; H, 6.34; N, 10.54. Found: C, 46.1; H, 6.18; N, 10.50.

EXAMPLE 7

Preparation of [3S,4aR,6S,8aR]-6-((5-ethoxycarbonyl-1H-imidazol-1-yl)methyl)-1,2,3,4,4a,5,6,7,8,8a-decahydroisoquinoline-3-carboxylic Acid Dihydrochloride.

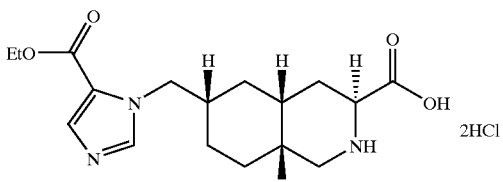

Scheme I, step E: A solution of 0.20 g of [3S,4aR,6S,8aR]-ethyl-6-((5-ethoxycarbonyl-1H-imidazol-1-yl)methyl)-1,2,3,4,4a,5,6,7,8,8a-decahydroisoquinoline-3-carboxylate dihydrochloride (prepared in example 5) in 10 mL of 5N HCl was heated at 50° C. for three hours and then at room temperature for 18 h. The solution was evaporated and vacuum dried at 50° C. to give 0.173 g of the title compound: MS m/z: 336.2 (m$^+$+1). Analysis calculated for C$_{17}$H$_{25}$N$_3$O$_4$.2HCl H$_2$O: C, 47.9; H, 6.9; N, 9.85. Found: C, 48.11; H, 7.66; N, 9.99.

EXAMPLE 8

Preparation of [3S,4aR,6S,8aR]-Ethyl-6-((5-carboxylic Acid-1H-imidazol-1-yl)methyl)-1,2,3,4,4a,5,6,7,8,8a-decahydroisoquinoline-3-carboxylate.

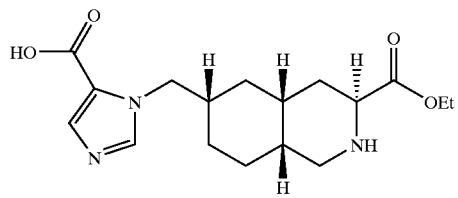

Scheme I, step F: To a suspension of 1.2 g of [3S,4aR,6S,8aR]-6-((5-carboxylic acid-1H-imidazol-1-yl)methyl)-1,2,3,4,4a,5,6,7,8,8a-decahydroisoquinoline-3-carboxylic acid dihydrochloride (prepared in example 6) in absolute ethanol was added 9.5 mL 1M HCl in diethyl ether. The reaction was heated at reflux overnight and evaporated. The residue was purified by strong cation exchange chromatography eluting with methanol followed by 0.8M ammonia in methanol. The purified material was recrystallized from isopropyl alcohol to give 0.320 g of the title compound: MS m/z: 334.2 (m$^-$1); Analysis calculated for C$_{17}$H$_{25}$N$_3$O$_4$.H$_2$O: C, 57.7; H, 7.15; N, 11.8. Found: C, 57.04; H, 7.34; N, 11.59.

EXAMPLE 9

Preparation of [3S,4aR,6S,8aR]-6-((4-ethoxycarbonyl-1H-imidazol-1-yl)methyl)-1,2,3,4,4a,5,6,7,8,8a-decahydroisoquinoline-3-carboxylic Acid Dihydrochloride.

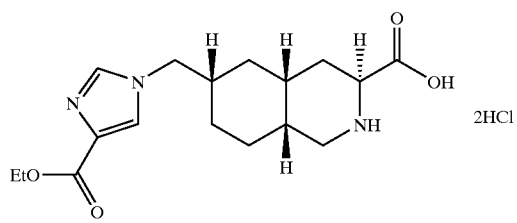

Scheme I, step E: A solution of 0.20 g of [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate (prepared in example 3) in 10 mL of 5N HCl was heated at 50° C. for three hours and then at room temperature for 18 h. The solution was evaporated and the resulting residue was chromatographed over C18 modified silica gel eluting with acetonitrile in aqueous 0.1% HCl to give 0.105 g of the title compound: MS m/z: 336 (m$^+$+1); Analysis calculated for C$_{17}$H$_{25}$N$_3$O$_4$HCl1.5H$_2$O: C, 51.2; H, 7.35; N, 10.55. Found: C, 51.33; H, 7.04; N, 10.62.

EXAMPLE 10

Preparation of [3S,4aR,6S,8aR]-Ethyl-6-((4-carboxylic Acid-1H-imidazol-1-yl)methyl)-1,2,3,4,4a,5,6,7,8,8a-decahydroisoquinoline-3-carboxylate Dihydrochloride.

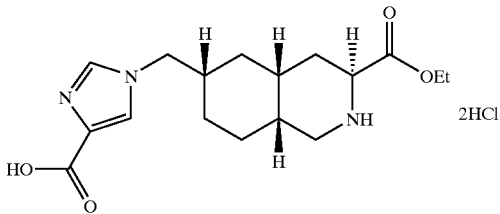

Scheme I, step F: To a suspension of 0.2 g of [3S,4aR,6S,8aR]-6-((4-Carboxylic acid-1H-imidazol-1-yl)methyl)-1,2,3,4,4a,5,6,7,8,8a-decahydroisoquinoline-3-carboxylic acid dihydrochloride (prepared in example 4) in absolute ethanol was added 9.5 mL 1M HCl in diethyl ether. The reaction was heated at reflux overnight, cooled and evaporated to dryness. The resulting residue was chromatographed over C18 modified silica gel eluting with acetonitrile in aqueous 0.1% HCl to give 0.165 g of the title compound: MS m/z: 336.2 (m$^+$+1); 400 MHz $^1$H NMR (CDCl$_3$) δ 8.4 (s, 1 H), 7.9 (s, 1 H), 4.3–4.2 (m, 2H), 4.1–4.0 (m, 3H), 3.25–3.2 (m, 1H), 3.1–3.0 (dd, 1H), 2.15–2.0 (m, 3H), 2.0–1.9 (m, 2H), 1.75–1.6 (m, 2H), 1.5–1.3 (m, 3H), 1.3–1.2 (t, 3H), 1.15–1.0 (m, 1H).

EXAMPLE 11

Preparation of [3S 4aR,6S,8aR]-Ethyl 6-{[4,5-Bis(ethoxycarbonyl)-1H-imidazol-1-yl]methyl}1 2,3,4,4a,5,6,7,8,8a-decahydroisoquinoline-3-carboxylate Dihydrochloride.

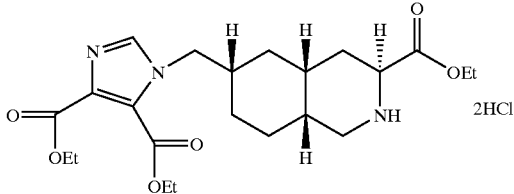

Preparation of [3S,4aR,6S ,8aR]-Ethyl-6-((4-nitrophenylsulfonyloxy)methyl)-2-(methoxycarbonyl)-1,2,3,4,4a,5,6,7,8,8a-decahydroisoquinoline-3-carboxylate.

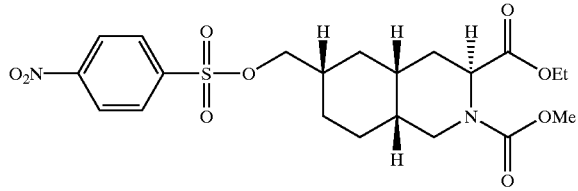

Scheme I, step A: A solution of [3S,4aR,6S,8aR]-ethyl-6-(hydroxymethyl)-2-(methoxycarbonyl)-1,2,3,4,4a,5,6,7,8,8a-decahydroisoquinoline-3-carboxylate (8.50 g, 0.0284 mol), triethylamine (8.62 g, 0.852 mol), 4-nitrobenzenesulfonyl chloride (6.49 g, 0.0284 mol), and dichloromethane (121 mL) was stirred at ambient temperature and monitored by tic (ethyl acetate/hexane 1:1/I2 stain). After three hours, additional 4-nitrobenzenesulfonyl chloride (0.63 g, 0.00284 mol) was added and the reaction stirred one additional hour at ambient temperature. The reaction mixture was concentrated to dryness. The residue was dissolved in ethyl acetate (121 mL) and filtered to remove triethylamine hydrochloride. The filtrate was washed with 1N hydrochloric acid solution (2×100 mL), saturated sodium bicarbonate solution (2×100 mL), and saturated sodium chloride solution (1×100 mL). The organic layer was dried using sodium sulfate, filtered, and concentrated to give 13.42 g (98%) of the intermediate title compound as an orange oil.

$^1$H nmr (CDCl$_3$): δ 1.15–1.29 (m, 5H), 1.44–1.69 (m, 5H), 1.78–1.94 (m, 3H), 2.08–2.17 (dt, 1H), 3.29–3.45 (m, 2H), 3.69 (s, 3H), 3.91–4.03 (m, 2H), 4.14–4.21 (q, 2H), 4.36–4.40 (t, 1H), 8.06–8.10 (dd, 2H), 8.38–8.41 (dd, 2H).

Preparation of [3S,4aR,6S,8aR]-Ethyl-6-((4,5-bis-ethoxycarbonyl-1H-imidazol-1-yl)methyl)-2-(methoxycarbonyl)-1,2,3,4,4a,5,6,7,8,8a-decahydroisoquinoline-3-carboxylate.

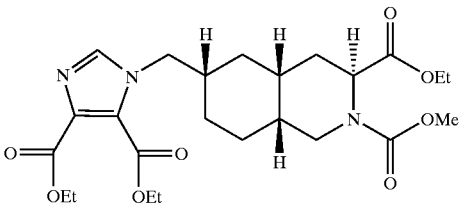

Scheme I, step B: A solution of [3S,4aR,6S,8aR]-ethyl-6-((4-nitrophenylsulfonyloxy)methyl)-2-(methoxycarbonyl)-1,2,3,4,4a,5,6,7,8,8a-decahydroisoquinoline-3-carboxylate (13.42 grams, 0.0277 mol), diethyl 4,5-imidazolecarboxylate [Y. S. Rhee, R. A. Jones, *J. Am. Chem. Soc.* 1990,112, 8174.] (11.70 g, 0.0554 mol), and N,N-dimethylformamide (83 mL) was heated for three hours at 60° C. until complete as determined by tic (hexane/ethyl acetate, 1:1). The reaction was cooled, diluted with saturated sodium bicarbonate (300 mL) and extracted with ethyl acetate (4×100 mL). The combined extracts were washed with 5% lithium chloride solution, dried using sodium sulfate, and concentrated to dryness. The residue was purified using Biotage Flash 40M (dichloromethane/methanol, 49:1) to give 10.87 g (79%) of the intermediate title compound as an amber oil.

$^1$H nmr (CDCl$_3$): δ 1.03–1.11 (q, 2H), 1.17–1.22 (t, 3H), 1.26–1.35 (m, 6H), 1.35–1.46 (m, 3H), 1.51–1.59 (m, 1H), 1.59–1.66 (m, 1H), 1.72–1.78 (m, 2H), 1.78–1.90 (t, 1H), 2.05–2.14 (m, 1H), 3.21–3.33 (m, 1H), 3.33–3.41 (dd, 1H), 3.64 (s, 3H), 3.97–4.08 (m, 2H), 4.08–4.15 (q, 2H), 4.26–4.35 (m, 5H), 7.42 (s, 1H). MS (FIA) m/z 494.3 ([M+H]$^+$)

Preparation of [3S,4aR,6S,8aR]-Ethyl-6-((4,5-bis-ethoxycarbonyl-1H-imidazol-1-yl)methyl)-1,2,3,4,4a,5,6,7,8,8a-decahydroisoquinoline-3-carboxylate.

Scheme I, step C: A solution of [3S,4aR,6S,8aR]-ethyl-6-((4,5-bis-ethoxycarbonyl-1H-imidazol-1-yl)methyl)-2-(methoxycarbonyl)-1,2,3,4,4a,5,6,7,8,8a-decahydroisoquinoline-3-carboxylate (10.55 g, 0.02138 mol), iodotrimethylsilane (21.39 g, 0.1069 mol), and dichloromethane (428 mL) was stirred for 16 hours at ambient temperature until complete as determined by tic (ethyl acetate/hexane, 2:1). The reaction mixture was concentrated to approximately 200 mL, ethanol (100 mL) was added and the resulting solution concentrated to a yellow foam. The residue was dissolved in methanol (190 mL) and stirred for 30 minutes with Amberlyst 15 resin (50 g). The resin was filtered and washed with methanol (100 mL). The product was eluted from the Amberlyst resin with 2N ammonia in methanol (2×100 mL). The filtrate was concentrated to an oil. The residue was purified by Biotage Flash 40M (dichloromethane/methanol, 19:1) to give 4.72 g of the free base of the final title compound, [3S,4aR,6S,8aR]-ethyl-6-((4,5-bis-ethoxycarbonyl-1H-imidazol-1-yl)methyl)-1,2,3,4,4a,5,6,7,8,8a-decahydroisoquinoline-3-carboxylate.

Preparation of [3S,4aR,6S,8aR]-Ethyl-6-((4,5-bis-ethoxycarbonyl-1H-imidazol-1-yl)methyl)-1,2,3,4,4a,5,6,7,8,8a-decahydroisoquinoline-3-carboxylate Dihydrochloride.

[3S,4aR,6S,8aR]-Ethyl-6-((4,5-bis-ethoxycarbonyl-1H-imidazol-1-yl)methyl)-1,2,3,4,4a,5,6,7,8,8a-decahydroisoquinoline-3-carboxylate was dissolved in ethyl acetate (50 mL) and a solution of 1.86M hydrochloric acid in ethyl acetate (11.65 mL, 0.0217 mol) was added giving a sticky solid. The reaction mixture was concentrated to dryness. The residue was dissolved in dichloromethane (10 mL) and added dropwise to diethyl ether (150 mL) causing the precipitation of 5.09 g (47%) of [3S,4aR,6S,8aR]-Ethyl-6-((4,5-bis-ethoxycarbonyl-1H-imidazol-1-yl)methyl)-1,2,3,4,4a,5,6,7,8,8a-decahydroisoquinoline-3-carboxylate dihydrochloride; mp 99–101° C.

$^1$H nmr(DMSO-d$_6$): δ 0.87–1.0 (q, 1H), 1.09–1.15 (d, 1H), 1.15–1.26 (m, 10H), 1.38–1.52 (m, 2H), 1.52–1.58 (d, 1H), 1.65–1.76 (s, broad, 1H), 1.76–1.89 (m, 3H), 2.04–2.13 (d, 1H), 2.47 (s, 1H), 2.91–2.99 (d, 1H), 2.99–3.08 (q, 1H), 3.94–4.09 (m, 3H), 4.16–4.31 (m, 6H), 7.92 (s, 1H), 9.18–9.29 (d, 1H), 9.63–9.72 (d, 1H). MS (FIA) m/z 436.3 ([M+H]$^+$).

Anal. Calcd. for $C_{22}H_{35}N_3O_6Cl_2$: C: 51.97; H: 6.94; N: 8.26. Found: C: 51.82; H: 7.02; N: 8.18.

EXAMPLE 12

Preparation of [3S,4aR,6S,8aR]-Ethyl-6-((4,5-dicarboxylic Acid-1H-imidazol-1-yl)methyl)-1,2,3,4,4a,5,6,7,8,8a-decahydroisoquinoline-3-carboxylate Dihydrochloride.

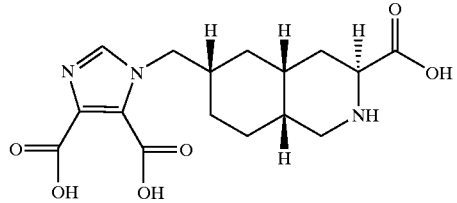

Scheme I, step D: To a solution of 0.15 g of [3S,4aR,6S,8aR]-Ethyl-6-((4,5-bis-ethoxycarbonyl-1H-imidazol-1-yl)methyl)-1,2,3,4,4a,5,6,7,8,8a-decahydroisoquinoline-3-carboxylate (prepared in example 11) in methanol at 20° C. was added 6.4 ml of a 1.0 M aqueous solution of lithium hydroxide. The resulting mixture was stirred for 18 h. Upon completion, the reaction was acidified to pH 4 with 1N HCl and evaporated to dryness. The crude product was purified by strong cation exchange chromatography eluting with 50% methanol in water followed by 10% pyridine in methanol/water (1:1) to provide [3S,4aR,6S,8aR]-ethyl-6-((4,5-dicarboxylic acid-1H-imidazol-1-yl)methyl)-1,2,3,4,4a,5,6,7,8,8a-decahydroisoquinoline-3-carboxylate.

Preparation of [3S,4aR,6S,8aR]-Ethyl-6-((4,5-dicarboxylic Acid-1H-imidazol-1-yl)methyl)-1,2,3,4,4a,5 6,7,8,8a-decahydroisoquinoline-3-carboxylate Dihydrochloride.

[3S,4aR,6S,8aR]-Ethyl-6-((4,5-dicarboxylic acid -1H-imidazol-1-yl)methyl)-1,2,3,4,4a,5,6,7,8,8a-decahydroisoquinoline-3-carboxylate was dissolved in water, treated with 1.5 ml of 1N HCl and evaporated to provide 0.65 g of [3S,4aR,6S,8aR]-ethyl-6-((4,5-dicarboxylic acid-1H-imidazol-1-yl)methyl)-1,2,3,4,4a,5,6,7,8,8a-decahydroisoquinoline-3-carboxylate dihydrochloride: MS m/z: 350.2 ([m–H]$^+$);

400 MHz $^1$H NMR (CD$_3$OD) δ 1.05 (bs, 1H), 1.25–1.67 (m, 5H), 1.85–2.17 (m, 5H), 3.00 (dd, 1H), 3.15 (d, 1H), 3.72 (d, 1H), 4.35 (dd, 2H), 7.75 (s, 1H).

To establish that the iGluR$_5$ receptor subtype is mediating neurogenic protein extravasation, a functional characteristic of migraine, the binding affinity of the compounds of formula I to the iGluR$_5$ receptor is first measured using standard methods. For example, the activity of compounds acting at the iGluR$_5$ receptor can be determined by radiolabelled ligand binding studies at the cloned and expressed human iGluR$_5$ receptor (Korczak et al., 1994, Recept. Channels 3; 41–49), and by whole cell voltage clamp electrophysiological recordings of currents in acutely isolated rat dorsal root ganglion neurons (Bleakman et al., 1996, Mol. Pharmacol. 49; 581–585). The selectivity of compounds acting at the iGluR$_5$ receptor subtype can then be determined by comparing antagonist activity at the iGluR$_5$ receptor with antagonist activity at other AMPA and kainate receptors. Methods useful for such comparison studies include: receptor-ligand binding studies and whole-cell voltage clamp electrophysiological recordings of functional activity at human GluR$_1$, GluR$_2$, GluR$_3$ and GluR$_4$ receptors (Fletcher et al., 1995, Recept. Channels 3; 21–31); receptor-ligand binding studies and whole-cell voltage clamp electrophysiological recordings of functional activity at human GluR$_6$ receptors (Hoo et al., Recept. Channels 2;327–338); and whole-cell voltage clamp electrophysiological recordings of functional activity at AMPA receptors in acutely isolated cerebellar Purkinje neurons (Bleakman et al., 1996, Mol. Pharmacol. 49; 581–585) and other tissues expressing AMPA receptors (Fletcher and Lodge, 1996, Pharmacol. Ther. 70; 65–89).

iGluR$_5$ Antagonist Binding Affinity Profiles

Cell lines (HEK293 cells) stably transfected with human iGluR receptors are employed. Displacement of $^3$[H] AMPA by increasing concentrations of antagonist is measured on iGluR$_1$, iGluR$_2$, iGluR$_3$, and iGluR$_4$ expressing cells, while displacement of $^3$[H] kainate (KA) is measured on iGluR$_5$, iGluR$_6$, iGluR$_7$, and KA2-expressing cells. As an indicia of selectivity, the ratio of binding affinity to the iGluR$_2$ AMPA receptor subtype, versus the binding affinity to iGluR$_5$ kainate receptor subtype, is also determined. As noted above, the compounds of the present invention display a surprisingly selective binding affinity for the iGluR$_5$ receptor. More specifically, the compounds of the present invention exhibit at least a 20 fold greater binding affinity for the iGluR$_5$ receptor than for iGluR$_2$ receptor.

In comparison, the binding affinity of:

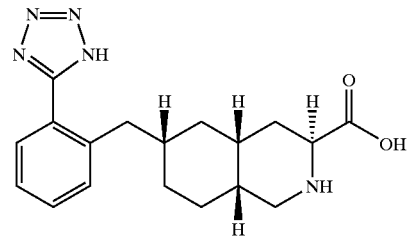

which is example 4 as disclosed in U.S. Pat. No. 5,446,051, displays only a 5 fold selectivity for the iGluR$_5$ receptor over the iGluR$_2$ receptor.

The ability of the compounds to treat migraine may be demonstrated as described in U.S. Pat. Nos. 5,817,671 and 5,792,763 and as described in *J. Neurosci. Methods*, 81(1,2) 19–24 (1998). For example, the following animal model is employed to determine the ability of each of the compounds of formula I to inhibit protein extravasation, an exemplary functional assay of the neuronal mechanism of migraine. The results obtained from this model are provided in Table I below.

Animal Model of Dural Protein Extravasation

Harlan Sprague-Dawley rats (225–325 g) or guinea pigs from Charles River Laboratories (225–325 g) are anesthetized with sodium pentobarbital intraperitoneally (65 mg/kg or 45 mg/kg respectively) and placed in a stereotaxic frame (David Kopf Instruments) with the incisor bar set at −3.5 mm for rats or −4.0 mm for guinea pigs. Following a midline sagital scalp incision, two pairs of bilateral holes are drilled through the skull (6 mm posteriorly, 2.0 and 4.0 mm laterally in rats; 4 mm posteriorly and 3.2 and 5.2 mm laterally in guinea pigs, all coordinates referenced to bregma). Pairs of stainless steel stimulating electrodes, insulated except at the tips (Rhodes Medical Systems, Inc.), are lowered through the holes in both hemispheres to a depth of 9 mm (rats) or 10.5 mm (guinea pigs) from dura.

The femoral vein is exposed and a dose of the test compound is injected intravenously (i.v.) at a dosing volume of 1 ml/Kg or, in the alternative, test compound is administered orally (p.o) via gavage at a volume of 2.0 ml/Kg. Approximately 7 minutes post i.v. injection, a 50 mg/Kg dose of Evans Blue, a fluorescent dye, is also injected intravenously. The Evans Blue complexes with proteins in the blood and functions as a marker for protein extravasation. Exactly 10 minutes post-injection of the test compound, the left trigeminal ganglion is stimulated for 3 minutes at a current intensity of 1.0 mA (5 Hz, 4 msec duration) with a Model 273 potentiostat/galvanostat (EG&G Princeton Applied Research).

Fifteen minutes following stimulation, the animals are killed and exsanguinated with 20 mL of saline. The top of the skull is removed to facilitate the collection of the dural membranes. The membrane samples are removed from both hemispheres, rinsed with water, and spread flat on microscopic slides. Once dried, the tissues are coverslipped with a 70% glycerol/water solution.

A fluorescence microscope (Zeiss) equipped with a grating monchromator and a spectrophotometer is used to quantify the amount of Evans Blue dye in each sample. An excitation wavelength of approximately 535 nm is utilized and the emission intensity at 600 nm was determined. The microscope is equipped with a motorized stage and also interfaced with a personal computer. This facilitates the computer-controlled movement of the stage with fluorescence measurements at 25 points (500 mm steps) on each dural sample. The mean and standard deviation of the measurements are determined by the computer.

The extravasation induced by the electrical stimulation of the trigeminal ganglion is an ipsilateral effect (i.e. occurs only on the side of the dura in which the trigeminal ganglion is stimulated). This allows the other (unstimulated) half of the dura to be used as a control. The ratio of the amount of extravasation in the dura from the stimulated side, over the amount of extravasation in the unstimulated side, is calculated. Control animals dosed with only with saline, yield a ratio of approximately 2.0 in rats and approximately 1.8 in guinea pigs. In contrast, a compound which effectively prevents the extravasation in the dura from the stimulated side would yield a ratio of approximately 1.0. A dose-response curve is generated for the compound and the dose that inhibits the extravasation by 50% ($ID_{50}$) or 100% ($ID_{100}$) is approximated. The $ID_{100}$ for the compound of example 3 given orally is 0.3 ng/Kg.

As used herein the term "patient" refers to a mammal, such a mouse, gerbil, guinea pig, rat, dog, monkey, or human. It is understood, however, that the preferred patient is a human.

As used herein, the terms "treating" or "to treat" each mean to alleviate symptoms, eliminate the causation of resultant symptoms either on a temporary or permanent basis, and to prevent, slow the appearance, or reverse the progression or severity of resultant symptoms of the named disorder. As such, the methods of this invention encompass both therapeutic and prophylactic administration.

As used herein the term "effective amount" refers to the amount or dose of the compound, upon single or multiple dose administration to the patient, which provides the desired effect in the patient under diagnosis or treatment.

An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the migraine involved; the response of the individual patient; the particular compound administered; the mode of administration; the bioavailability characteristics of the preparation administered; the dose regimen selected; the use of concomitant medication; and other relevant circumstances.

A typical daily dose will contain from about 0.01 mg/kg to about 100 mg/kg of each compound used in the present method of treatment. Preferably, daily doses will be about 0.05 mg/kg to about 50 mg/kg, more preferably from about 0.1 mg/kg to about 25 mg/kg.

In effecting treatment of a patient afflicted with a condition, disease or disorder described herein, a compound of formula I can be administered in any form or mode which makes the compound bioavailable in effective amounts, including oral and parenteral routes. For example, compounds of formula I can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the disease state to be treated, the stage of the disease, and other relevant circumstances.

The selective $iGluR_5$ antagonists for use according to the methods of the present invention may be a single compound or a combination of compounds capable of functioning as a selective $iGluR_5$ receptor antagonist. For example, it may be a combination of a compound capable of functioning as an antagonist at the $iGluR_5$ receptor and one or more other glutamate receptors, in combination with one or more compounds capable of blocking its actions at the $iGluR_2$ receptor. It is understood, however, that the selective $iGluR_5$ antagonist for use in the methods of the present invention, is preferably a single compound.

Pharmaceutical Compositions

Oral administration is a preferred route of administering the compounds employed in the present invention whether administered alone, or as a combination of compounds capable of acting as a selective $iGluR_5$ receptor antagonist. Oral administration, however, is not the only route, nor even the only preferred route. Other preferred routes of administration include transdermal, percutaneous, intravenous, intramuscular, intranasal, buccal, or intrarectal routes. Where the selective iGluR$_5$ receptor antagonist is administered as a combination of compounds, one of the compounds may be administered by one route, such as oral, and the other may be administered by the transdermal, percutaneous, intravenous, intramuscular, intranasal, buccal, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating said compounds are important embodiments of the present invention. Such compositions may take any physical form which is pharmaceutically acceptable, but orally administered pharmaceutical compositions are particularly preferred. Such pharmaceutical compositions contain an effective amount of a selective iGluR$_5$ receptor antagonist, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compound, however, is best defined as the "effective amount", that is, the amount of each compound which provides the desired dose to the patient in need of such treatment. The activity of the compounds employed in the present invention do not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following table provides an illustrative list of formulations suitable for use with the compounds employed in the present invention. The following is provided only to illustrate the invention and should not be interpreted as limiting the present invention in any way.

Formulation 1
Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2
A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3
An aerosol solution is prepared containing the following components:

| | Weight % |
|---|---|
| Active Ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

Formulation 4
Tablets each containing 60 mg of active ingredient are made as follows:

| Active Ingredient | 60 mg |
|---|---|
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

Formulation 5
Capsules each containing 80 mg medicament are made as follows:

| Active Ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 sieve, and filled into hard gelatin capsules in 200 mg quantities.

Formulation 6
Suppositories each containing 225 mg of active ingredient may be made as follows:

| Active Ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7
Suspensions each containing 50 mg of medicament per 5 ml dose are made as follows:

| Active Ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8
An intravenous formulation may be prepared as follows:

| Active Ingredient | 100 mg |
|---|---|
| Mannitol | 100 mg |

-continued

Formulation 8
An intravenous formulation may be prepared as follows:

| | |
|---|---|
| 5 N Sodium hydroxide | 200 ml |
| Purified water to total | 5 ml |

As with any group of structurally related compounds which possess a particular generic utility, certain groups and configurations are preferred for compounds of formula I.

With respect to substituent W, compounds wherein W is hydrogen, methyl, or $CO_2H$ are preferred, with hydrogen being most preferred.

With respect to substituent X, compounds wherein X is hydrogen, methyl, or $CO_2H$ are preferred, with $CO_2H$ being most preferred.

With respect to $R^1$, compounds wherein $R^1$ is hydrogen or $C_1$–$C_{20}$ alkyl are preferred, compounds wherein $R^1$ is $C_1$–$C_4$ alkyl are most preferred, and compounds wherein $R^1$ is methyl or ethyl are most especially preferred.

With respect to $R^2$, compounds wherein $R^2$ is hydrogen or $C_1$–$C_{20}$ alkyl are preferred, compounds wherein $R^2$ is $C_1$–$C_4$ alkyl are most preferred, and compounds wherein $R^2$ is methyl or ethyl are most especially preferred.

With respect to $R^3$, compounds wherein $R^3$ is hydrogen, $C_1$–$C_{20}$ alkyl are preferred, compounds wherein $R^3$ is $C_1$–$C_4$ alkyl are most preferred, and compounds wherein $R^3$ is methyl or ethyl are most especially preferred.

In particular, compounds of formula Ie:

formula Ie

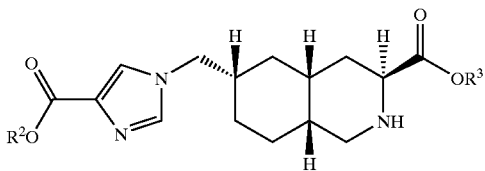

wherein $R^2$ and $R^3$ are each independently hydrogen, methyl or ethyl, are especially preferred.

We claim:

1. A compound of the formula:

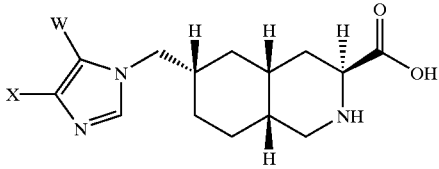

wherein

W represents hydrogen, $C_1$–$C_4$ alkyl, —$CH_2CO_2H$, or $CO_2H$; and

X represents hydrogen, $C_1$–$C_4$ alkyl, —$CH_2CO_2H$, or $CO_2H$;

with the proviso that at least one of W or X must be other than hydrogen;

or a prodrug or a pharmaceutically acceptable salt thereof.

2. The compound according to claim 1 wherein W represents hydrogen.

3. The compound according to claim 1 wherein X represents hydrogen.

4. The compound according to claim 3 wherein W represents $CO_2H$.

5. A compound which is [3S,4aR,6S,8aR]-6-((4-carboxylic acid-1H-imidazol-1-yl)methyl)-1,2,3,4,4a,5,6,7,8,8a-decahydroisoquinoline-3-carboxylic acid or a pharmaceutically acceptable salt thereof.

6. A compound according to claim 5 wherein the pharmaceutically acceptable salt is the dihydrochloride.

7. A compound of the formula:

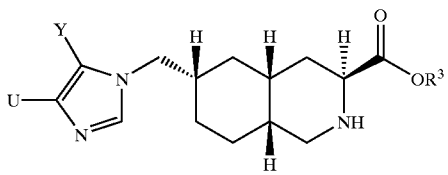

wherein

Y represents hydrogen, $C_1$–$C_4$ alkyl, —$CH_2CO_2R^1$, or $CO_2R^1$;

U represents hydrogen, $C_1$–$C_4$ alkyl, —$CH_2CO_2R^2$, or $CO_2R^2$; and $R^1$, $R^2$ and $R^3$ each independently represent hydrogen, $C_1$–$C_{20}$ alkyl, $C_2$–$C_6$ alkenyl, $C_1$–$C_6$ alkylaryl, $C_1$–$C_6$ alkyl($C_3$–$C_{10}$)cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, or $C_1$–$C_6$ alkyl-morpholine;

or a pharmaceutically acceptable salt thereof, with the proviso that at least one of Y or U is other than hydrogen or $C_1$–$C_4$ alkyl, and with the further proviso that at least one of $R^1$, $R^2$ or $R^3$ is other than hydrogen.

8. The compound according to claim 7 wherein U is $CO_2R^2$.

9. The compound according to claim 8 wherein $R^2$ and $R^3$ are each independently $C_1$–$C_{20}$ alkyl.

10. The compound according to claim 9 wherein $R^2$ and $R^3$ are each independently $C_1$–$C_4$ alkyl.

11. The compound according to claim 7 wherein U is hydrogen.

12. The compound according to claim 11 wherein Y is $CO_2R^1$.

13. The compound according to claim 12 wherein $R^1$ and $R^3$ are each independently $C_1$–$C_{20}$ alkyl.

14. The compound according to claim 13 wherein $R^1$ and $R^3$ are each independently $C_1$–$C_4$ alkyl.

15. The compound according to claim 14 wherein $R^1$ and $R^3$ are each independently methyl or ethyl.

16. A compound which is [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate or a pharmaceutically acceptable salt thereof.

17. A compound according to claim 16 which is [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate dihydrochloride.

18. A compound according to claim 16 which is [3S,4aR,6S,8aR]-ethyl-6-((4-ethoxycarbonyl-1H-imidazol-1-yl)methyl)-1,2,3,4,4a,5,6,7,8,8a-decahydroisoquinoline-3-carboxylate citrate.

19. A method of treating migraine which comprises administering to a patient an effective amount of a compound according to claim 1.

20. A pharmaceutical composition comprising an effective amount of a compound according to claim 1 in combination with a pharmaceutically acceptable carrier, diluent or excipient.

21. A process for preparing a compound of formula Id:

formula Id

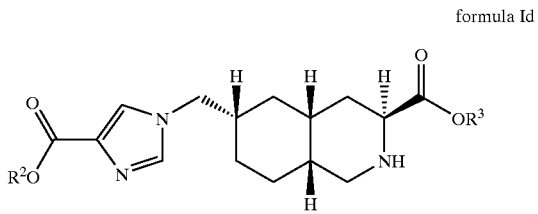

wherein $R^2$ and $R^3$ each independently represent $C_1$–$C_{20}$ alkyl, $C_2$–$C_6$ alkenyl, $C_1$–$C_6$ alkylaryl, $C_1$–$C_6$ alkyl($C_3$–$C_{10}$) cycloalkyl, $C_1$–$C_6$ alkyl-N,N-$C_1$–$C_6$ dialkylamine, $C_1$–$C_6$ alkyl-pyrrolidine, $C_1$–$C_6$ alkyl-piperidine, or $C_1$–$C_6$ alkyl-morpholine;

comprising combining a compound of structure (3a):

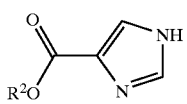

(3a)

wherein $R^2$ is defined as above, with a suitable base in a suitable solvent, followed by addition of a compound of structure (2):

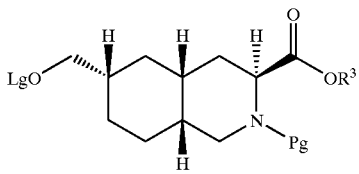

(2)

wherein $R^3$ is defined as above, Pg is a suitable nitrogen protecting group, and OLg is a suitable leaving group, followed by removal of the nitrogen protecting group.

* * * * *